(12) United States Patent
Zhou et al.

(10) Patent No.: US 9,814,886 B2
(45) Date of Patent: Nov. 14, 2017

(54) DETECTING AND TREATING ELECTROMECHANICAL DISSOCIATION OF THE HEART

(75) Inventors: Xiaohong Zhou, Woodbury, MN (US); Paul G. Krause, Shoreview, MN (US); William T. Donofrio, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 2205 days.

(21) Appl. No.: 12/697,019

(22) Filed: Jan. 29, 2010

(65) Prior Publication Data

US 2010/0198284 A1 Aug. 5, 2010

Related U.S. Application Data

(60) Provisional application No. 61/148,674, filed on Jan. 30, 2009.

(51) Int. Cl.
*A61N 1/00* (2006.01)
*A61N 1/362* (2006.01)
(Continued)

(52) U.S. Cl.
CPC ........ *A61N 1/3627* (2013.01); *A61N 1/36114* (2013.01); *A61N 1/3962* (2013.01);
(Continued)

(58) Field of Classification Search
CPC A61N 1/3627; A61N 1/36114; A61N 1/3962; A61N 1/0551; A61N 1/36557; A61N 1/36564
(Continued)

(56) References Cited

U.S. PATENT DOCUMENTS

| 4,374,382 A | 2/1983 | Markowitz |
| 4,987,897 A | 1/1991 | Funke |

(Continued)

FOREIGN PATENT DOCUMENTS

| EP | 0688577 A1 | 12/1995 |
| EP | 1857141 A1 | 11/2007 |

(Continued)

OTHER PUBLICATIONS

A. Niijima, D.L. Winter. The Effect of Catecholamines on Unit Activities in Afferent Nerves from the Adrenal Glands. J. Phsyiol. (1968), 195, pp. 647-656.*

(Continued)

*Primary Examiner* — Lindsey G Wehrheim

(57) ABSTRACT

In some examples, an electromechanical disassociation state (EMD) of a heart of a patient can be treated by delivering electrical stimulation to a tissue site to at least one of modulate afferent nerve activity or inhibit efferent nerve activity upon determining that the heart is in an electromechanical dissociation state, where the tissue site comprises at least one of a nonmyocardial tissue site or a nonvascular cardiac tissue site. The delivery of electrical stimulation may effectively treat the EMD state of the heart, e.g., by enabling effective mechanical contraction of the heart. In another example, an electromechanical disassociation state of a heart of a patient can be treated by determining autonomic nervous system activity associated with a detected EMD state of the heart of a patient, and delivering electrical stimulation therapy to the patient based on the determined autonomic nervous system activity of the patient associated with the EMD state.

27 Claims, 15 Drawing Sheets

(51) Int. Cl.
*A61N 1/36* (2006.01)
*A61N 1/39* (2006.01)
*A61N 1/05* (2006.01)
*A61N 1/365* (2006.01)

(52) U.S. Cl.
CPC ........ *A61N 1/0551* (2013.01); *A61N 1/36557* (2013.01); *A61N 1/36564* (2013.01)

(58) Field of Classification Search
USPC ........... 607/4–38, 119–132, 2; 600/373–375, 600/449–450, 481–503, 508–528
See application file for complete search history.

(56) References Cited

U.S. PATENT DOCUMENTS

| | | | |
|---|---|---|---|
| 5,117,824 A | 6/1992 | Keimel et al. | |
| 5,261,400 A | 11/1993 | Bardy | |
| 5,292,338 A | 3/1994 | Bardy | |
| 5,388,586 A | 2/1995 | Lee et al. | |
| 5,545,186 A | 8/1996 | Olson et al. | |
| 5,755,736 A | 5/1998 | Gillberg et al. | |
| 6,134,470 A * | 10/2000 | Hartlaub | 607/14 |
| 6,473,644 B1 | 10/2002 | Terry, Jr. et al. | |
| 7,010,345 B2 | 3/2006 | Hill et al. | |
| 7,076,283 B2 | 7/2006 | Cho et al. | |
| 7,096,064 B2 | 8/2006 | Deno et al. | |
| 7,218,964 B2 | 5/2007 | Hill et al. | |
| 2001/0001126 A1 | 5/2001 | Cammilli et al. | |
| 2004/0030365 A1* | 2/2004 | Rubin | 607/60 |
| 2004/0254612 A1* | 12/2004 | Ezra et al. | 607/5 |
| 2005/0149133 A1 | 7/2005 | Libbus et al. | |
| 2005/0197675 A1 | 9/2005 | David et al. | |
| 2005/0197680 A1 | 9/2005 | DelMain et al. | |
| 2006/0095080 A1 | 5/2006 | Libbus et al. | |
| 2006/0116737 A1 | 6/2006 | Libbus | |
| 2006/0241699 A1 | 10/2006 | Libbus et al. | |
| 2006/0271115 A1* | 11/2006 | Ben-Ezra et al. | 607/5 |
| 2006/0271118 A1 | 11/2006 | Libbus et al. | |
| 2007/0043393 A1 | 2/2007 | Brockway et al. | |
| 2007/0150011 A1 | 6/2007 | Meyer et al. | |
| 2007/0208381 A1 | 9/2007 | Hill et al. | |
| 2007/0213773 A1 | 9/2007 | Hill et al. | |
| 2007/0239215 A1 | 10/2007 | Bhunia et al. | |
| 2007/0239229 A1 | 10/2007 | Masoud et al. | |
| 2007/0260283 A1 | 11/2007 | Li | |
| 2007/0260285 A1 | 11/2007 | Libbus et al. | |
| 2007/0299477 A1* | 12/2007 | Kleckner et al. | 607/9 |
| 2008/0015659 A1 | 1/2008 | Zhang et al. | |
| 2008/0021507 A1 | 1/2008 | Libbus et al. | |
| 2008/0051839 A1 | 2/2008 | Libbus et al. | |
| 2008/0097535 A1* | 4/2008 | Ideker et al. | 607/6 |
| 2008/0147140 A1 | 6/2008 | Ternes et al. | |
| 2008/0167696 A1 | 7/2008 | Cates et al. | |
| 2008/0215118 A1 | 9/2008 | Goetz et al. | |
| 2009/0026201 A1 | 1/2009 | Hall et al. | |
| 2009/0163969 A1 | 6/2009 | Donofrio | |

FOREIGN PATENT DOCUMENTS

| | | |
|---|---|---|
| WO | 0066222 A1 | 11/2000 |
| WO | 03020364 A2 | 3/2003 |
| WO | 2004110550 A2 | 12/2004 |
| WO | 2005063332 A1 | 7/2005 |
| WO | 2006119131 A1 | 11/2006 |
| WO | 2008073235 A1 | 6/2008 |

OTHER PUBLICATIONS

International Preliminary Report on Patentability from international application No. PCT/US2010/022618, dated Aug. 11, 2011, 9 pp.

Siu et al., "Inappropriate Implantable Cardioverter Defibrillator Shock from a Transcutaneous Muscle Stimulation Device Therapy" Journal of Interventional Cardiac Electrophysiology 13:73-75, 2005.

U.S. Appl. No. 61/148,674, filed Jan. 30, 2009, "Detecting and Treating Electromechanical Disassociation of the Heart", by Zhou et al.

U.S. Appl. No. 61/110,300, filed Oct. 31, 2008, "Implantable Medical Device Crosstalk Evaluation and Mitigation", by Burnes et al.

U.S. Appl. No. 12/362,768, filed Jan. 30, 2009, "Implantable Medical Device Crosstalk Evaluation and Mitigation", by Burnes et al.

U.S. Appl. No. 11/963,045, filed Dec. 21, 2007, "Optical Sensor and Method for Detecting a Patient Condition," by Donofrio et al.

International Search report and Written Opinion of international application No. PCT/US2010/022618, dated Apr. 9, 2010, 15 pp.

* cited by examiner

DETECTING AND TREATING ELECTROMECHANICAL DISSOCIATION OF THE HEART

This application claims the benefit of U.S. Provisional Application No. 61/148,674, entitled, "DETECTING AND TREATING ELECTROMECHANICAL DISSOCIATION OF THE HEART," and filed on Jan. 30, 2009, the entire content of which is incorporated herein by reference.

TECHNICAL FIELD

The disclosure relates to medical devices and, in particular, medical devices configured to deliver electrical stimulation therapy to a patient.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry.

For example, implantable cardiac devices, such as cardiac pacemakers or implantable cardioverter defibrillators, provide therapeutic stimulation to the heart by delivering electrical signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation therapy to the heart of the patient upon detecting ventricular tachycardia, and deliver cardioversion or defibrillation therapy to a patient's heart upon detecting ventricular fibrillation. Some medical device systems that include a neurostimulator in addition to implantable cardiac device have also been proposed.

SUMMARY

In general, the disclosure is directed to therapy systems for treating the electromechanical dissociation (EMD) of a heart of a patient. In an EMD state, the heart of the patient exhibits what may be considered typical electrical activity (e.g., a normal sinus rhythm observed in an electrogram or electrocardiogram), but does not exhibit proper mechanical contractions. In some examples, a therapy system detects an EMD state of the heart of the patient based on one or more sensed physiological parameters of a patient that indicate whether the heart is sufficiently contracting. The therapy system may be configured to sense such physiological parameters in conjunction with the delivery of cardioversion or defibrillation therapy by a cardiac device. The heart may be susceptible to entering an EMD state after delivery of such cardioversion or defibrillation therapy.

When the therapy system determines that the heart of a patient is in an EMD state, the therapy system generates and delivers electrical stimulation to a tissue site of the patient to modulate afferent nerve activity and/or inhibit efferent nerve activity. Such electrical stimulation may be configured to effectively treat the EMD state, e.g., by promoting mechanical contraction of the heart. The therapy system may deliver the electrical stimulation to one or more tissue sites including least one of a nonmyocardial tissue site or a nonvascular cardiac tissue site.

In some examples, the therapy system may monitor autonomic nervous system activity of a patient. When the therapy system determines that the heart of a patient is in an EMD state, the therapy system determines autonomic activity (e.g., sympathetic and/or parasympathetic nervous system activity) associated with the EMD state. Electrical stimulation delivered to the patient to treat the EMD state may then be determined based on the autonomic activity associated with the EMD state. For example, the therapy system may determine that a relatively low level of sympathetic nervous system activity is exhibited by the patient during the occurrence of the EMD state. In such an example, the therapy system may deliver electrical stimulation to the patient configured to increase sympathetic nervous system activity in the patient. In this manner, as the autonomic nervous system activity associated with the EMD state may be an underlying cause of the EMD state, the stimulation delivered to the patient may effectively treat the EMD state based on the autonomic nervous system activity associated with the detected EMD state.

In one example, the disclosure is directed to a method comprising sensing at least one physiological parameter of a patient, determining whether a heart of the patient is in an electromechanical dissociation state based on the at least one sensed physiological parameter, and delivering electrical stimulation to a tissue site of the patient to at least one of modulate afferent nerve activity or inhibit efferent nerve activity upon determining that the heart is in the electromechanical dissociation state, wherein the tissue site comprises at least one of a nonmyocardial tissue site or a nonvascular cardiac tissue site.

In another example, the disclosure is directed to a medical system comprising a sensor that senses at least one physiological parameter of a patient, a processor that determines whether a heart of the patient is in an electrical mechanical dissociation state based on the at least one sensed physiological parameter, and a stimulation generator that delivers electrical stimulation to a tissue site of the patient to at least one of modulate afferent nerve activity or inhibit efferent nerve activity when the processor determines that the heart is in the electrical mechanical dissociation state, wherein the tissue site comprises at least one of a nonmyocardial tissue site or a nonvascular cardiac tissue site.

In another example, the disclosure is directed to a medical system comprising means for sensing at least one physiological parameter of a patient, means for determining whether a heart of the patient is in an electrical mechanical dissociation state of a heart of the patient based on the at least one sensed physiological parameter, and means for delivering electrical stimulation to a tissue site of the patient to at least one of modulate afferent nerve activity or inhibit efferent nerve activity upon determining that the heart is in the electrical mechanical dissociation state, wherein the tissue site comprises at least one of a nonmyocardial tissue site or a nonvascular cardiac tissue site.

In another example, the disclosure is direct to a method of treating an electromechanical disassociation state of a heart of a patient, wherein the method is characterized by implanting a medical device system in a patient, where the medical device system comprises a stimulation generator and a processor that determines whether the heart of the patient is in the electrical mechanical dissociation state based on at least one sensed physiological parameter and controls the stimulation generator to deliver electrical stimulation to a tissue site of the patient to at least one of modulate afferent nerve activity or inhibit efferent nerve activity upon determining that the heart is in the electrical mechanical dissociation state, wherein the tissue site comprises at least one of a nonmyocardial tissue site or a nonvascular cardiac tissue site.

In another example, the disclosure is directed to a method comprising determining whether a heart of a patient is in an electromechanical dissociation state, determining autonomic activity of the patient associated with the electromechanical dissociation state, and delivering electrical stimulation to the patient based on the determined autonomic activity of the patient associated with the electromechanical dissociation state.

In another example, the disclosure is directed to a medical system comprising a processor that determines whether a heart of the patient is in an electrical mechanical dissociation state and that determines autonomic activity of the patient associated with the electromechanical dissociation state, and a stimulation generator that delivers electrical stimulation to the patient based on the determined autonomic activity of the patient associated with the electromechanical dissociation state.

In another example, the disclosure is directed to a medical system comprising means for determining whether a heart of a patient is in an electromechanical dissociation state, means for determining autonomic activity of the patient associated with the electromechanical dissociation state, and means for delivering electrical stimulation to the patient based on the determined autonomic activity of the patient associated with the electromechanical dissociation state.

In another example, the disclosure is directed to a method of treating an electromechanical disassociation state of a heart of a patient, wherein the method is characterized by implanting a medical device system in a patient, where the medical device system comprises a stimulation generator, and a processor that determines whether a heart of a patient is in an electrical mechanical dissociation state, determines autonomic nervous system activity of the patient associated with the electromechanical dissociation state upon determining that the heart is in the electromechanical dissociation state, and controls the stimulation generator to deliver electrical stimulation to the patient based on the determined autonomic nervous system activity of the patient associated with the electromechanical dissociation state.

The details of one or more examples are set forth in the accompanying drawings and the description below. Other features, objects, and advantages of the devices, systems, and techniques of the disclosure will be apparent from the description and drawings, and from the claims.

DETAILED DESCRIPTION

Figure 1:
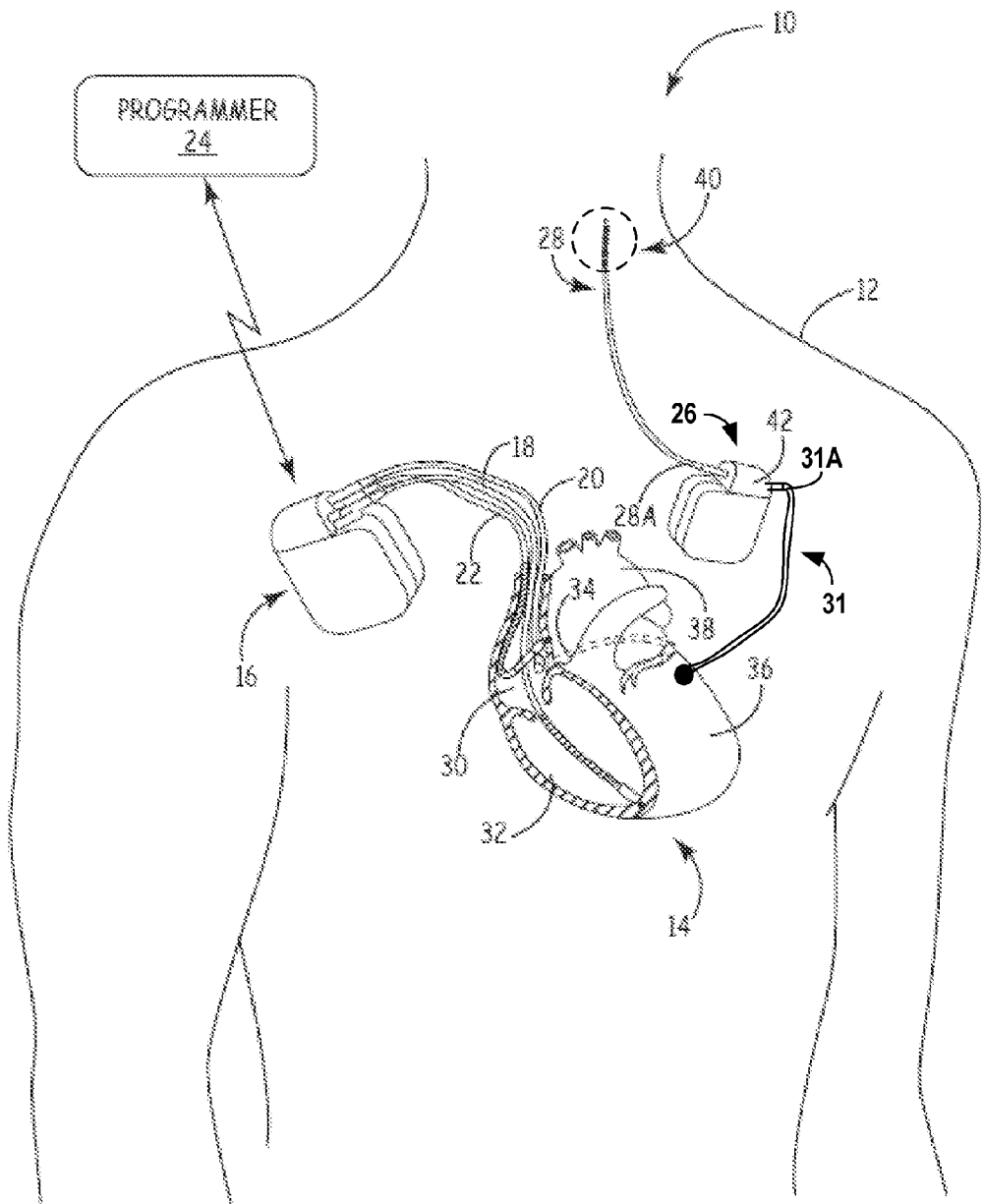
FIG. 1 is a conceptual diagram illustrating an example therapy system that includes an implantable cardiac device (ICD) and an implantable neurostimulator (INS).

FIG. 1 is a conceptual diagram illustrating an example therapy system 10 that may be used to provide therapy to patient 12. Therapy system 10 includes implantable cardiac device (ICD) 16, which is connected to leads 18, 20, and 22, and programmer 24. ICD 16 may comprise, for example, an implantable pacemaker, cardioverter, and/or defibrillator that provide therapy to heart 14 of patient 12 via electrodes connected to one or more of leads 18, 20, and 22. In some examples, ICD 16 may deliver pacing pulses, but not cardioversion or defibrillation pulses, while in other examples, ICD 16 may deliver cardioversion or defibrillation pulses, but not pacing pulses. In addition, in further examples, ICD 16 may deliver pacing, cardioversion, and defibrillation pulses.

In some examples, ICD 16 may not deliver cardiac rhythm management therapy to heart 14, but may instead only sense electrical cardiac signals of heart 14 and/or other physiological parameters of patient 12 (e.g., blood oxygen saturation, blood pressure, temperature, heart rate, respiratory rate, and the like), and store the electrical cardiac signals and/or other physiological parameters of patient 12 for later analysis by a clinician. In such examples, ICD 16 may be referred to as a patient monitoring device. Examples of patient monitoring devices include, but are not limited to, the Reveal Plus Insertable Loop Recorder, which is available from Medtronic, Inc. of Minneapolis, Minn. For ease of description, ICD 16 will be referred to herein as a cardiac rhythm management therapy delivery device.

Therapy system 10 further comprises implantable electrical stimulator 26, which is coupled to lead 28 and 31. Electrical stimulator 26 may also be referred to as an implantable neurostimulator (INS) 26. INS 26 may be any suitable implantable medical device (IMD) that includes a signal generator that generates electrical stimulation signals that may be delivered to a tissue site of patient 12, e.g., tissue proximate a vagus nerve, a spinal cord or heart 14 of patient 12. Although INS 26 is referred to throughout the remainder of the disclosure as a "neurostimulator" and as delivering neurostimulation pulses, in other examples, INS 26 may deliver electrical stimulation to any suitable nonmyocardial tissue site within patient 12, which may or may not be proximate a nerve.

In some examples, INS 26 may deliver stimulation signals to any suitable tissue site to modulate the activity of the autonomic nervous system of patient 12, e.g., parasympathetic, sympathetic and/or neurohormonal activity. For example, based on autonomic activity associated with an detected electromechanical disassociation (EMD) state of heart 14, INS 26 may deliver stimulation signals to any suitable tissue site to increase or decrease sympathetic nervous system activity. In other examples, INS 26 may deliver electrical stimulation signals to any suitable tissue site to at least one of modulate afferent nerve activity or inhibit efferent nerve activity upon determining that the heart is in the EMD state.

In some examples, the target tissue site for therapy delivery by INS 26 may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. An extravascular tissue site may be outside of heart 14 and outside of arteries, veins, or other vasculature of patient 12. In other examples, stimulation may be delivered to a nonmyocardial tissue site via electrodes of an intravascular lead that is implanted within vasculature. A nonvascular cardiac tissue site may include, for example, a cardiac fat pad.

In some examples, INS 26 may deliver electrical stimulation therapy to a nerve of patient 12 via a lead implanted within vasculature (e.g., a blood vessel) of patient 12. In some examples, INS 26 may deliver electrical stimulation that is delivered to peripheral nerves that innervate heart 14, or fat pads on heart 14 that may contain nerve bundles. In the example shown in FIG. 1, electrodes of lead 28 are positioned outside the vasculature of patient 12 and positioned to deliver electrical stimulation to a vagus nerve (not shown) of patient 12.

In some examples, delivery of electrical stimulation by INS 26 to a nonmyocardial tissue site or nonvascular cardiac tissue site may help modulate an autonomic nervous system of patient 12 and/or provide cardioprotective benefits to patient 12. For example, delivery of electrical stimulation to a tissue site proximate a nerve of patient 12 may help treat heart failure. In addition, delivery of electrical stimulation to a tissue site proximate a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma. In some examples, delivery of electrical stimulation to a tissue site proximate a nerve of patient 12 to modulate autonomic nervous system activity may help treat heart 14 when in an EMD state. Delivery of electrical stimulation by INS 26 may complement antitachycardia therapy (e.g., antitachycardia pacing, cardioversion or defibrillation) by ICD 16 or provide backup therapy to the cardiac rhythm therapy provided by ICD 16. For example, if ICD 16 is unavailable to provide therapy to patient 12, e.g., due to a low power level, INS 26 may deliver therapy to patient 12 to help terminate or prevent a cardiac event (e.g., tachycardia).

As described in further detail below, INS 26 may also deliver therapy to modulate afferent nerve activity and/or inhibit efferent nerve activity of patient 12 in order to treat EMD of heart 14. In general, EMD, which also may be known as pulseless electrical activity (PEA), refers to a patient condition characterized by the persistence of electrical activity in heart 14 without associated mechanical contraction, with minimal mechanical contraction or substantially ineffective mechanical contraction. EMD may be described as a clinical condition characterized by unresponsiveness and lack of palpable pulse in the presence of organized cardiac electrical activity. In some cases, heart 14 may be prone to enter an EMD state after the delivery of cardioversion or defibrillation therapy, e.g., by ICD 16, as previously described, although it is not limited to such situations.

When heart 14 is in an EMD state, the electrical activity of heart 14 may be indicative of a heart functioning in a manner that includes mechanical contraction. For example, an electrocardiogram (ECG) or electrogram (EGM) of heart 14 may indicate a sinus rhythm of heart 14. However, despite the presence of relatively normal electrical activity, heart 14 may not be mechanically contracting in a physiologically significant manner. Physiologically significant mechanical contractions may be, for example, contractions necessary to supply the cardiac output (e.g., sufficient blood flow) to meet the needs of the patient's body. Thus, although heart 14 may produce weak contractions when in an EMD state, the contractions that produce the blood perfusion necessary to sustain life are not present despite the persistence of electrical activity in heart 14. In some cases, EMD may be associated with the presence of electrical activity and the absence of cardiac contractions.

In some examples, EMD may not be readily detectable by only monitoring the electrical activity of the heart of a patient. Accordingly, in order to detect EMD of heart 14, therapy system 10 may include one or more sensors that sense physiological parameters that indicate whether heart 14 is contracting in a physiologically significant manner. Examples of physiological parameters that may indicate the extent to which heart 14 is contracting include blood pressure, blood flow, blood oxygen saturation level, movement of cardiac muscles, heart sounds corresponding to contraction, heart images (e.g., based on implantable ultrasonic techniques), tissue perfusion and the like.

In some examples, INS 26 sense one or more physiological parameters of patient 12 that indicate the relative level of heart contraction. The sensed physiological parameter may be used to determine when heart 14 is in an electromechanical dissociation (EMD) state. If INS 26 determines that heart 14 is in an EMD state, INS 26 may deliver stimulation therapy to patient 12 in order to terminate the EMD state of heart 14. The stimulation therapy modulates afferent nerve activity and/or inhibits efferent nerve activity of patient 12 in order to terminate the EMD state. The electrical stimulation therapy may be delivered by INS 26 to a tissue site of patient 12, such as, e.g., nonmyocardial tissue site or a nonvascular cardiac tissue site.

In the example shown in FIG. 1, INS 26 may sense one or more physiological parameter via one or more sensors of lead 31, where the sensors are located proximate to heart 14. In some examples, ICD 16 may additionally, or alternatively, sense one or more physiological parameters of patient 12 that may be used to determine whether heart 14 is in an EMD state. In addition, system 10 may include a sensing device separate than that of ICD 16 and INS 26 that senses one or more physiological parameters used to determine when heart 14 is in an EMD state.

As described in further detail below, in some examples, INS 26 and/or ICD 16 monitors autonomic nervous system activity of patient 12 to determine autonomic nervous system activity associated with an EMD state of heart 14. The autonomic nervous system associated with a detected EMD state of heart 14 of patient 12 can be the state of the autonomic nervous system at the time the EMD state is detected, at a time preceding the detection of the EMD state (e.g., preceding the EMD state detection by a predetermined period of time), or at a time following the detection of the EMD state. In examples described herein, the autonomic nervous system associated with a detected EMD state of heart 14 of patient 12 includes at least the state of the autonomic nervous system activity at the time ICD 16 or INS 26 detected the EMD state of patient 12. Autonomic nervous system activity of patient 12 may include sympathetic nervous system activity and/or parasympathetic nervous system activity.

In some examples, the behavior of autonomic nervous system activity may be an underlying cause of the EMD state in patient 12. In one example, depressed sympathetic nervous system activity may cause heart 14 to enter or maintain an EMD state, while in other examples, overexcited sympathetic nervous system activity may cause heart 14 to enter or maintain an EMD state. As such, upon detecting that heart 14 is in an EMD state, INS 26 and/or ICD 16 may determine the whether the EMD state is accompanied by relatively low or high level of sympathetic or other autonomic nervous system activity. As discussed in further detail with respect to FIGS. 14 and 15, ICD 16 and/or INS 26 or another device can determine whether sympathetic activity of patient 12 is relatively high or low by comparing one or more physiological parameters to threshold values associated with the relatively low and relatively high sympathetic activity designations.

The autonomic activity associated with a detected EMD state may be used to select the type (e.g., as indicated by stimulation parameter values or target stimulation sites) of electrical stimulation delivered to patient 12 by INS 26 (or ICD 16) to treat the EMD state. For example, if depressed sympathetic nervous system activity is associated with a detected EMD state, INS 26 may deliver electrical stimulation to patient 12 configured to increase sympathetic nervous system activity. Conversely, if overexcited sympathetic nervous system activity is associated with a detected EMD state, INS 26 may deliver electrical stimulation to patient 12 configured to decrease sympathetic nervous system activity.

INS 26 and/or ICD 16 may monitor and determine autonomic nervous system activity of patient 12 using any suitable technique. In some examples, electrical activity of heart 14 may be sensed by ICD 16 and/or INS 26 (e.g., an electrocardiogram (ECG) or electrogram (EGM)) via one or more electrodes on leads 18, 20, 22, 28, 29 to identify autonomic activity associated with (e.g., temporally correlated with) a detected EMD state. For example, sensed electrical activity of heart 14 may be analyzed by INS 26, ICD 16 or other device to determine the heart rate of heart 14. Sensed electrical activity of heart 14 that reflects a relatively low heart rate, such as, e.g., about 20 to 30 beats per minute (BPM) compared to a "normal" heart rate of about 60 to about 70 BPM, may be indicate depressed sympathetic activity. Similarly, sensed electrical activity of heart 14 that reflects a relatively high heart rate, such as, e.g., about 100 to 120 beats per minute (BPM), may be indicate overexcited sympathetic activity. The low heart rate, high heart rate, and/or normal heart rate may be predetermined and stored by ICD 16, INS 26 or another device. In other examples, the normal heart may be determined based on, for example, an average sensed heart rate for a predetermined period of time preceding the detection of the EMD state. In this way, the "normal" heart rate may be a dynamically changing value.

Additionally or alternatively, heart rate variability (e.g., P-P interval variability and/or R-R interval variability) may also be analyzed by INS 26, ICD 16 or other device to monitor autonomic activity to treat the detected EMD state of patient 14. P-P or R-R interval variability refers to the variability in the P-P or R-R interval, i.e., the duration of time between consecutive or successive P or R waves, respectively. In some examples, sensed electrical activity of heart 14 that reflects an increase in heart rate variability may indicate overexcited parasympathetic nervous system activity. In this way, heart rate variability may be used as an indicator for the nature of the autonomic nervous system activity associated with a detected EMD state.

Additionally or alternatively, ICD 16 and/or INS 26 may determine autonomic nervous system activity associated with a detected EMD state of heart 14 by monitoring electrical activity at one or more nerve sites of patient 12 via one or more electrodes on leads 18, 20, 22, 28, 29. For example, INS 26 may monitor electrical activity of one or more sympathetic or parasympathetic ganglion of patient 12 via one or more of leads 28, 29. Similarly, ICD 16 or INS 26 may monitor electrical activity of the AV node, which may include a large number of parasympathetic nerve fibers. As such, electrical activity monitored at the AV node may be used as an indicator of excited or depressed parasympathetic nervous system activity. Sensed electrical activity from one or more nerve sites may be analyzed by ICD 16 and/or INS 26 to identify depressed or overexcited autonomic nervous system activity that may be associated with an EMD state of patient 12.

Based on the autonomic activity determined to be associated with the occurrence of a detected EMD state, INS 26 and/or ICD 16 may deliver electrical stimulation to patient 12 that appropriately modulates autonomic nervous system activity of patient 12. In this way, ICD 16 and/or INS 26 controls the delivery of stimulation to patient 12 based on the autonomic nervous system activity determined to be associated with the occurrence of a detected EMD state. In some examples, INS 26 stimulates the central nervous system to modulate parasympathetic and/or sympathetic activity. For example, INS 26 may stimulate spinal cord 44 of the central nervous system, e.g., in the cervical, thoracic, and/or lumbar regions. Additionally or alternatively, INS 26 may deliver peripheral nerve stimulation to patient 12 to module autonomic nervous system activity.

INS 26 may stimulate parasympathetic and/or sympathetic ganglia neural tissue of the central nervous system proximate to spinal cord 44. Stimulating one or more ganglion may allow INS 26 to deliver lower intensity stimulation, e.g., lower amplitude and/or lower frequency, than stimulating tissue of the peripheral nervous system further away from spinal cord 44. Additionally, in some cases, ganglia may be more convenient to access than peripheral neural tissue further away from spinal cord 44. For example, implanting leads 28 and 29 proximate to one or more ganglion may be less invasive than implanting leads 28 and proximate to other peripheral neural tissue further away from spinal cord 44.

Additionally or alternatively, INS 26 may stimulate the brain of patient 12, e.g., at one or more centers that regulate autonomic activity, such as the dorsal vagal motonucleus, nucleus ambiguus, nucleus tractus solitarii, hypothalamus, and/or spinal intermediolateral column. In such examples, one or more of leads 28 and 29 may be implanted within the brain of patient 12. Stimulation sites other than those describe herein are contemplated.

The components of ICD 16 and INS 26 are enclosed in separate housings, such that ICD 16 and INS 26 are physically separate devices. In other examples, the functionality of ICD 16 and INS 26 may be performed by an IMD that includes both a cardiac therapy module that generates and delivers at least one of pacing, cardioversion or defibrillation therapy to patient 12 and an electrical stimulation therapy module that generates and delivers electrical stimulation to a target tissue site within patient 12, which may be proximate a nerve, a nonvascular cardiac tissue site, an extravascular tissue site that is not proximate a nerve.

Leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As described in further detail with reference to FIG. 5, in other examples, an ICD may deliver stimulation therapy to heart 14 by delivering stimulation to a nonmyocardial tissue site in addition to or instead of delivering stimulation via electrodes of intravascular leads 18, 20, 22.

ICD 16 may sense electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22.

ICD 16 may detect arrhythmia of heart 14, such as fibrillation of ventricles 32 and 36, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 detects fibrillation employing one or more fibrillation detection techniques known in the art.

In the example of FIG. 1, INS 26 has been implanted in patient 12 proximate to an nonmyocardial target stimulation site 40, such as a tissue site proximate a vagus nerve. For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector 42 of INS 26 either directly or indirectly (e.g., via a lead extension). In particular, conductors disposed in the lead body may electrically connect stimulation electrodes (and sense electrodes, if present) of lead 28 to INS 26. Connector 42 may also be referred to as a connector block or a header of INS 26. Proximal end 31A of lead 31 may be both electrically and mechanically coupled to connector 42 of INS 26 either directly or indirectly (e.g., via a lead extension). When electrically coupled to INS 26, sensed information may be communicated from the sensor of lead 31 to INS 26.

INS 26 may also be referred to as a signal generator. In some examples, lead 28 may also carry one or more sense electrodes to permit INS 26 to sense electrical signals from target stimulation site 40. Furthermore, in some examples, INS 26 may be coupled to two or more leads, e.g., for bilateral or multi-lateral stimulation.

In other examples, electrodes of lead 28 may be positioned to deliver electrical stimulation to any other suitable nerve, which may be selected to be a nerve that may be modulated to change afferent nerve activity and/or inhibit efferent nerve activity of patient 12 in order to increase the contractility of heart 14. In addition, in other examples, electrodes of lead 28 or another lead electrically connected to INS 26 may be positioned to deliver stimulation to an organ, muscle or muscle group in patient 12, which may be selected based on, for example, a therapy regimen selected for a particular patient. For example, INS 26 may also deliver electrical stimulation to a target tissue site 40 that is not proximate to a nerve. For example, in some examples, INS 26 may deliver electrical stimulation to a peripheral nerve field site, whereby electrodes 124 (FIG. 7) of lead 28 are implanted in a region where patient 12 experiences pain. The pain may be related to stimulation delivered by ICD 16 or a patient condition, such as angina or chronic back pain. As other examples, INS 26 may deliver electrical stimulation to a muscle, muscle group, organ, or other sites that may not be proximate a nerve. Thus, while "neurostimulation" signals are primarily referred to herein, the disclosure is also applicable to examples in which INS 26 delivers electrical stimulation to other tissue sites.

Figure 2:
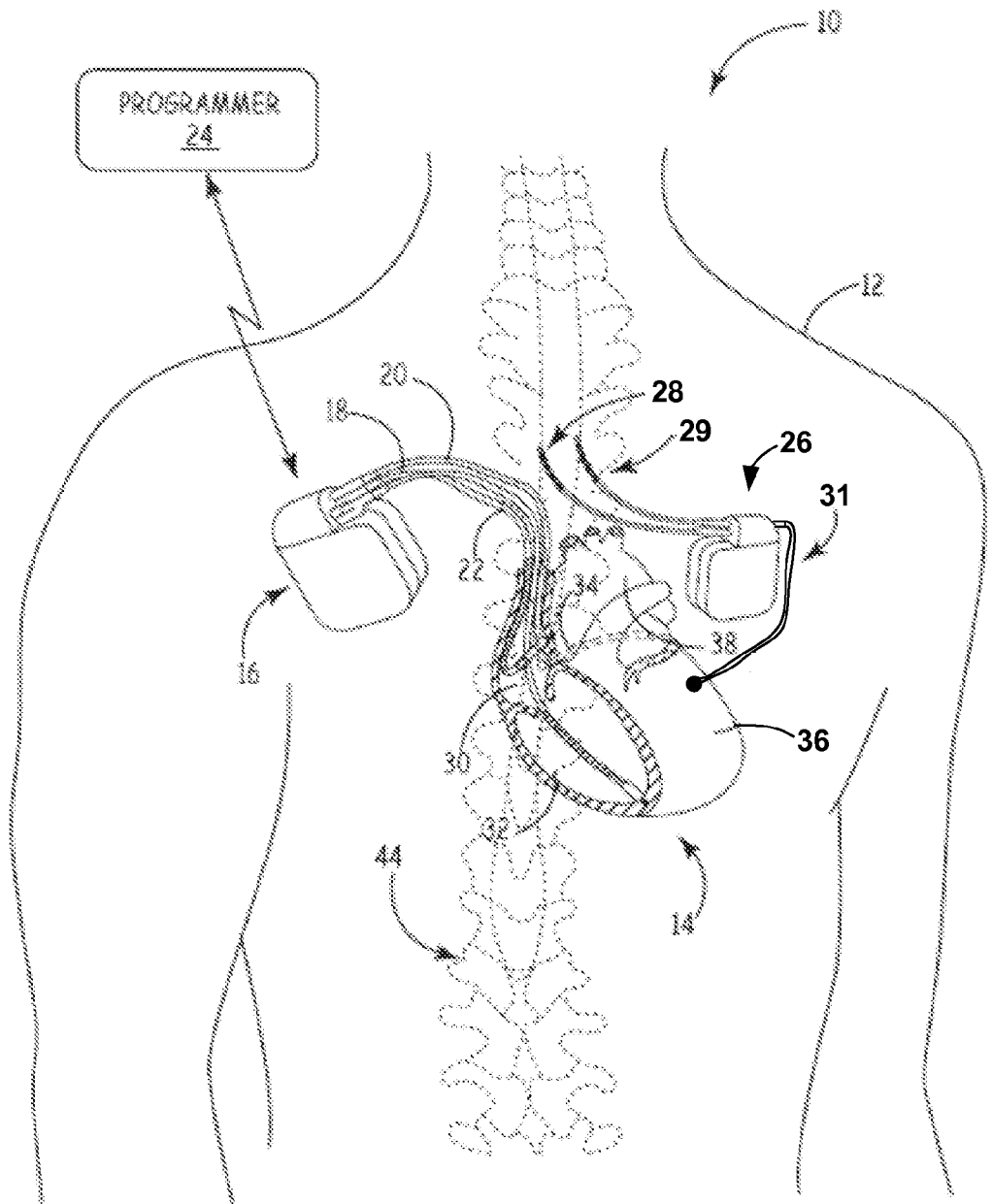
FIG. 2 is a conceptual diagram illustrating another example therapy system that includes an ICD and an INS.

As shown in FIG. 2, INS 26 may deliver electrical stimulation to spinal cord 44 of patient 12 in order to help modulate an afferent nerve of patient 12, inhibit efferent nerve activity of patient 12, or modulate autonomic nervous system activity to improve contractility of heart 14. In addition, stimulation of spinal cord 44 or nerves branching therefrom by INS 26 may help prevent or mitigate occurrences of tachyarrhythmias and may facilitate reduction of the level of aggressiveness of the cardiac therapy, such as pacing, cardioversion or defibrillation therapy, delivered by ICD 16. In this way, ICD 16 and INS 26 may operate in conjunction with each other to help prevent arrhythmias of heart 14 of patient 12, as well as to terminate detected arrhythmias. In some examples, INS 26 may deliver electrical stimulation during the cardiac refractory period or blanking period to avoid interfering with the cardiac sensing function of ICD 16.

In some examples, depending upon the neurostimulation target, the delivery of electrical stimulation by INS 26 may also mitigate perceptible discomfort generated from the delivery of pacing pulses or cardioversion/defibrillation shocks by ICD 16. For example, if INS 26 delivers electrical stimulation to spinal cord 44 of patient 12, the neurostimulation may produce paresthesia, which may help reduce the discomfort felt by patient 12 from the delivery of stimulation by ICD 16.

In the example shown in FIG. 2, INS 26 is coupled to two leads 28, 29 which may facilitate bilateral spinal cord stimulation of patient 12. Leads 28, 29 may be introduced into spinal cord 44 in the thoracic region, as shown in FIG. 2. In other examples, leads 28, 29 may be introduced into spinal cord 44 in the cervical or lumbar region. Electrodes of leads 28, 29 may be positioned within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

In some examples, INS 26 delivers therapy to patient 12 with a voltage amplitude of about 0.2 volts to about 12 volts, a pulse duration of about 40 microseconds (μs) to about 600 μs, such as about 50 μs to about 500 μs), and a pulse rate of approximately 1 Hertz (Hz) to approximately 1 kilohertz (e.g., 10 Hz to 100 Hz). However, other stimulation parameter values for INS 26 are contemplated. INS 26 may deliver electrical stimulation to patient 12 substantially continuously or periodically. In some examples, INS 26 may deliver electrical stimulation to patient 12 based on the timing of electrical stimulation by ICD 16, such as prior to the delivery of electrical stimulation (e.g., antitachycardia pacing or a defibrillation or cardioversion pulse) by ICD 16, during the delivery of electrical stimulation by ICD 16, subsequent to the delivery of electrical stimulation by ICD 16 or any combination of the aforementioned times.

In addition, in some examples, INS 26 may deliver electrical stimulation to patient 12 based on a sensed event or, such as atrial or ventricular depolarization, or based on a sensed physiological condition that indicates that heart 14 is in an EMD state. The event or physiological condition may be sensed by ICD 16, INS 26 or another sensing device. In some examples, the electrical stimulation used to treat the EMD state of heart 14 is configured to modulate afferent nerve activity and/or inhibit efferent nerve activity. In some examples, the electrical stimulation used to treat the EMD state of heart 14 is configured to modulate autonomic nervous system activity, where the type of modulation (e.g., in increase or decrease sympathetic activity) is based on the autonomic nerve activity determined to be associated with the EMD state.

ICD 16 and INS 26 may communicate with each other in order for INS 26 to time the delivery of electrical stimulation based on the delivery of stimulation pulses by ICD 16, where the stimulation pulses may be pacing pulses or cardioversion/defibrillation pulses. ICD 16 and INS 26 may communicate directly or indirectly (e.g., via an intermediate device, such as programmer 24) using any suitable communication technique. Examples communication techniques that may be implemented to facilitate communication between ICD 16 and INS 26 may include, for example, electrical signals transmitted through the patient's tissue, radiofrequency (RF) communication techniques, optical communication techniques, ultrasonic communication techniques, and the like. Communication between ICD 16 and INS 26 may be periodic, e.g., according to a regular schedule, or on an as-needed basis, e.g., when ICD 16 delivers cardiac rhythm management therapy to patient 12.

In other examples, INS 26 may deliver electrical stimulation to patient 12 independently of the cardiac rhythm therapy delivered by ICD 16. For example, INS 26 may be programmed to deliver electrical stimulation to patient 12 when EMD is detected based on one or more sensed physiological parameters of patient 12.

The values for the therapy parameters that define the electrical stimulation delivered by INS 26 may be organized into a group of parameter values referred to as a "therapy program" or "therapy parameter set." "Therapy program" and "therapy parameter set" are used interchangeably herein. In the case of electrical stimulation, the therapy parameters may include an electrode combination, an amplitude, which may be a current or voltage amplitude, and a frequency, and, if INS 26 delivers electrical pulses, a pulse width, and a pulse rate for stimulation signals to be delivered to the patient. An electrode combination may include a selected subset of one or more electrodes of lead 28, as well as lead 29 if INS 26 is connected to two leads 28, 29. The electrode combination may also refer to the polarities of the electrodes in the selected subset. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset. In some cases, INS 26 may deliver stimulation to patient 12 according to a program group that includes more than one therapy program. The stimulation signals according to the different therapy programs in a therapy group may be delivered on a time-interleaved basis or substantially simultaneously.

The electrical stimulation parameters may also include a duty cycle of stimulation signals, a timing of the delivery of the electrical stimulation relative to a cardiac cycle of heart 14 of patient 12, and a waveform shape or a signal envelope of the electrical stimulation signal. A signal envelope may generally traces the outline of the amplitude of a stimulation signal for a given period of time. The signal envelope may characterize the amplitude ramp-up and ramp-down times, which may be gradual or abrupt.

If INS 26 delivers therapy to patient 12 according to two or more electrode combinations, e.g., according to a therapy program group including two or more therapy programs defining at least two different electrode combinations, time-interleaving the stimulation signals defined each of the therapy programs may result in stimulation that is sequentially applied to different electrodes.

In some examples, the therapy parameter values with which INS 26 generates electrical stimulation therapy for patient 12 may be selected based on an effect the stimulation has on heart 14. For example, INS 26 may deliver stimulation to a tissue site within patient 12 according to a first therapy program defining values for a set of therapy parameters, and ICD 16 or INS 26 may assess the response of heart 14 or other portions of the cardiovascular system to the delivery of stimulation by INS 26. For example, after therapy delivery by INS 26 according to a first therapy program, INS 26 may sense one or more physiological parameters of patient 12 to determine whether heart 14 is mechanically contracting in a physiologically significant manner. Example physiological parameters that indicate heart 14 is mechanically contracting in a physiologically significant manner include, for example, blood pressure, blood flow, tissue perfusion, blood oxygen saturation level, movement of cardiac muscles, heart sounds, heart images, and tissue perfusion. The therapy program may be analyzed based on a positive or negative response of the mechanical activity of heart 14 to the delivery of stimulation by INS 26. The therapy program may be selected for storage in INS 26, e.g., for chronic therapy delivery if the test stimulation via the therapy program evoked a positive response by heart 14 and/or other portions of the patient's cardiovascular system.

Programmer 24 of FIGS. 1 and 2 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (e.g., EGM or ECG signals), intracardiac or intravascular pressure, activity, posture, respiration, heart sounds, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by ICD 16, such as cardioversion or pacing therapies. In some examples, the user may activate certain features of ICD 16 by entering a single command via programmer 24, such as depression of a single key or combination of keys of a keypad or a single point-and-select action with a pointing device.

The user may use programmer 24 to retrieve information from INS 26 regarding the performance or integrity of INS 26 or leads 28, 29, 30 (if INS 26 is connected to more than one lead) or a power source of INS 26. With the aid of programmer 24 or another computing device, a user may select values for therapy parameters for controlling therapy delivery by INS 26. The values for the therapy parameters may be organized into a group of parameter values referred to as a "therapy program" or "therapy parameter set." "Therapy program" and "therapy parameter set" are used interchangeably herein.

Programmer 24 may communicate with ICD 16 and INS 26 via wireless communication using any techniques known in the art. Examples of communication techniques may include, for example, low frequency or RF telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

Figure 3:
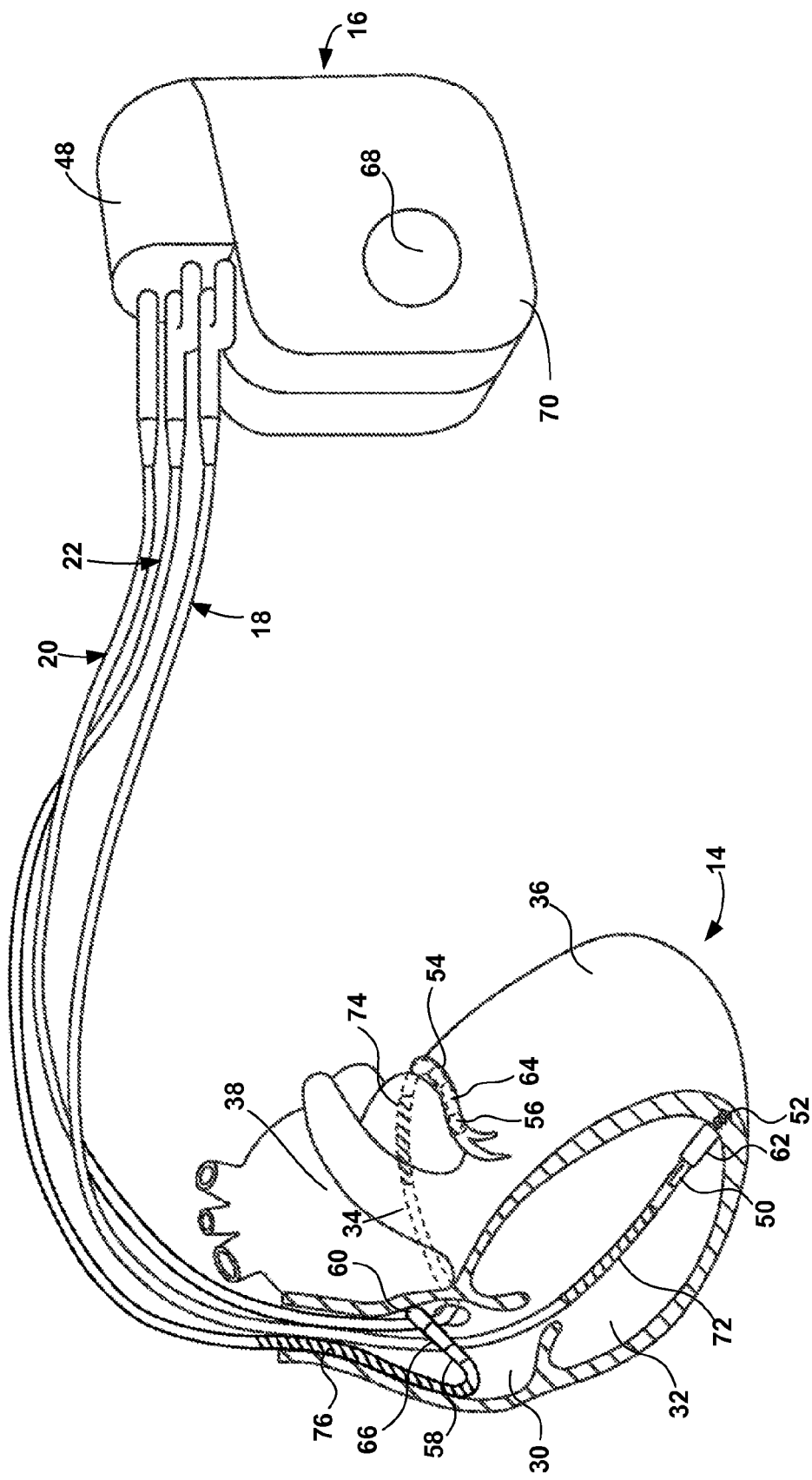
FIG. 3 is a conceptual diagram illustrating the ICD and associated leads of the therapy systems of FIGS. 1 and 2 in greater detail.

FIG. 3 is a conceptual diagram illustrating ICD 16 and leads 18, 20, 22 of therapy system 10 in greater detail. Leads 18, 20, 22 may be electrically coupled to a stimulation generator, a sensing module, or other modules ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54 and 58 may take the form of ring electrodes, and electrodes 52, 56 and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the conductors within the lead body of its associated lead 18, 20, 22, and thereby coupled to respective ones of the electrical contacts on the proximal end of leads 18, 20 and 22.

Electrodes 50, 52, 54, 56, 58, and 60 may sense electrical signals attendant to the depolarization and repolarization of heart 14. The electrical signals are conducted to ICD 16 via the respective leads 18, 20, 22. In some examples, ICD 16 also delivers pacing pulses via electrodes 50, 52, 54, 56, 58, and 60 to cause depolarization of cardiac tissue of heart 14. In some examples, as illustrated in FIG. 3, ICD 16 includes one or more housing electrodes, such as housing electrode 68, which may be formed integrally with an outer surface of hermetically-sealed housing 70 of ICD 16 or otherwise coupled to housing 70. In some examples, housing electrode 68 is defined by an uninsulated portion of an outward facing portion of housing 70 of ICD 16. Divisions between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 6, housing 70 may enclose a stimulation generator that generates cardiac pacing pulses and defibrillation or cardioversion shocks, as well as a sensing module for monitoring the patient's heart rhythm. In some examples, housing electrode 68 may be used to deliver neurostimulation signals to a nerve site of patient 12.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

The configurations of therapy system 10 illustrated in FIGS. 1-3 are merely examples. In other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14 or via external patch electrodes. In examples in which INS 26 is not implanted in patient 12, INS 26 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. Other examples of therapy systems may include three transvenous leads located as illustrated in FIGS. 1 and 3, and an additional lead located within or proximate to left atrium 38. Other examples of therapy systems may include a single lead that extends from ICD 16 into a chamber of heart 14, such as right atrium 30, right ventricle 32 or left ventricle 36, or two leads that extend into a respective one of the right ventricle 26 and right atrium 28. An example of this type of therapy system is shown in FIG. 4.

Figure 4:
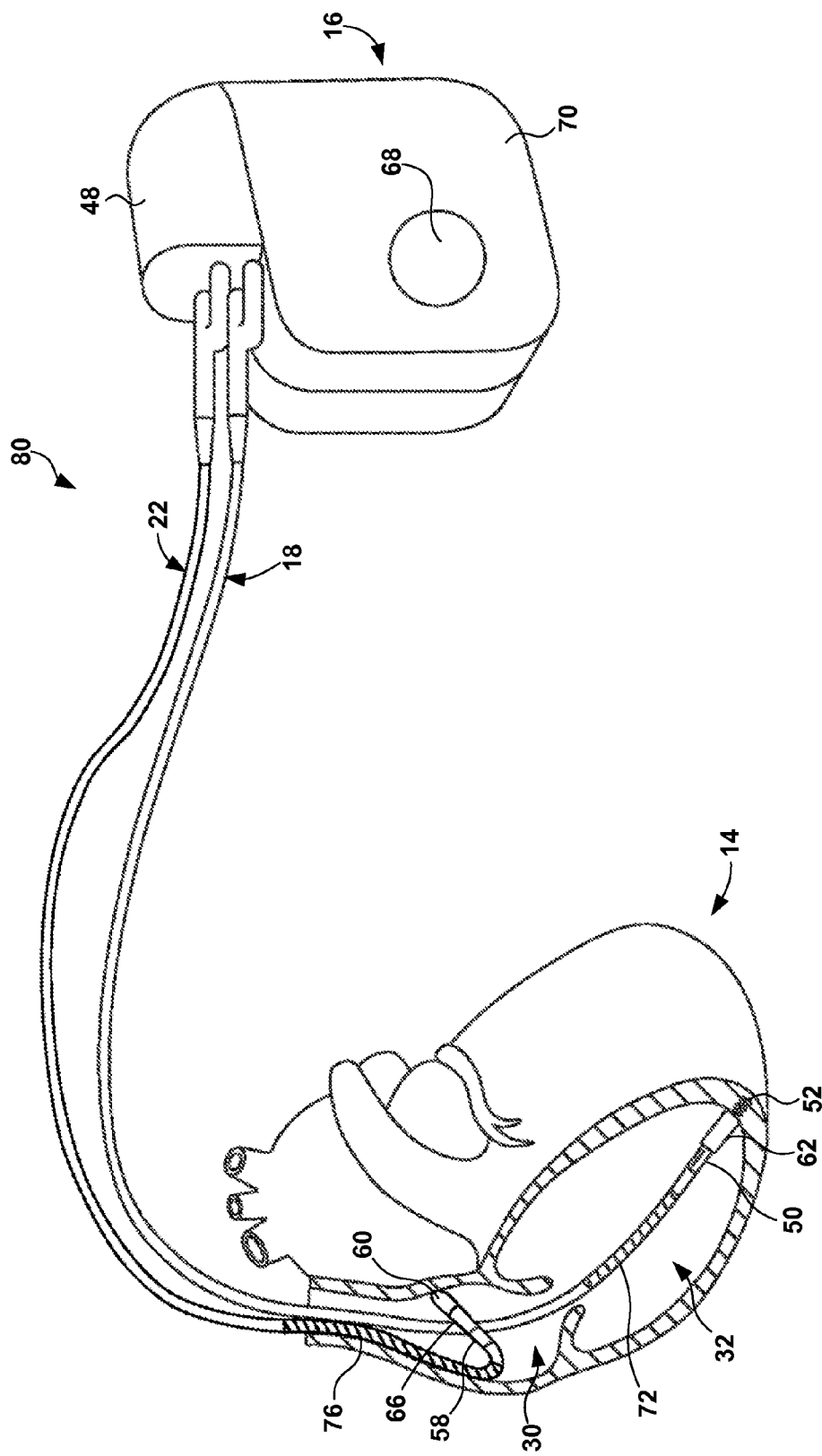
FIG. 4 is a conceptual diagram illustrating another example ICD lead configuration.

FIG. 4 is a conceptual diagram illustrating another example of therapy system 78, which includes ICD 16 connected to two leads 18, 22, rather than three leads as shown in FIGS. 1-3. Leads 18, 22 are implanted within right ventricle 32 and right atrium 30, respectively. Therapy system 78 shown in FIG. 4 may be useful for providing defibrillation and pacing pulses to heart 14. Therapy system 78 may further include INS 26 (not shown in FIG. 4), which is configured to deliver electrical stimulation therapy to modulate an autonomic nervous system of patient 12, (e.g., via stimulation of a vagus nerve or within spinal cord 44) in order to help prevent or mitigate an arrhythmia of patient 12 or to help improve the quality of mechanical contractions of heart 14 when in an EMD state.

Figure 5:
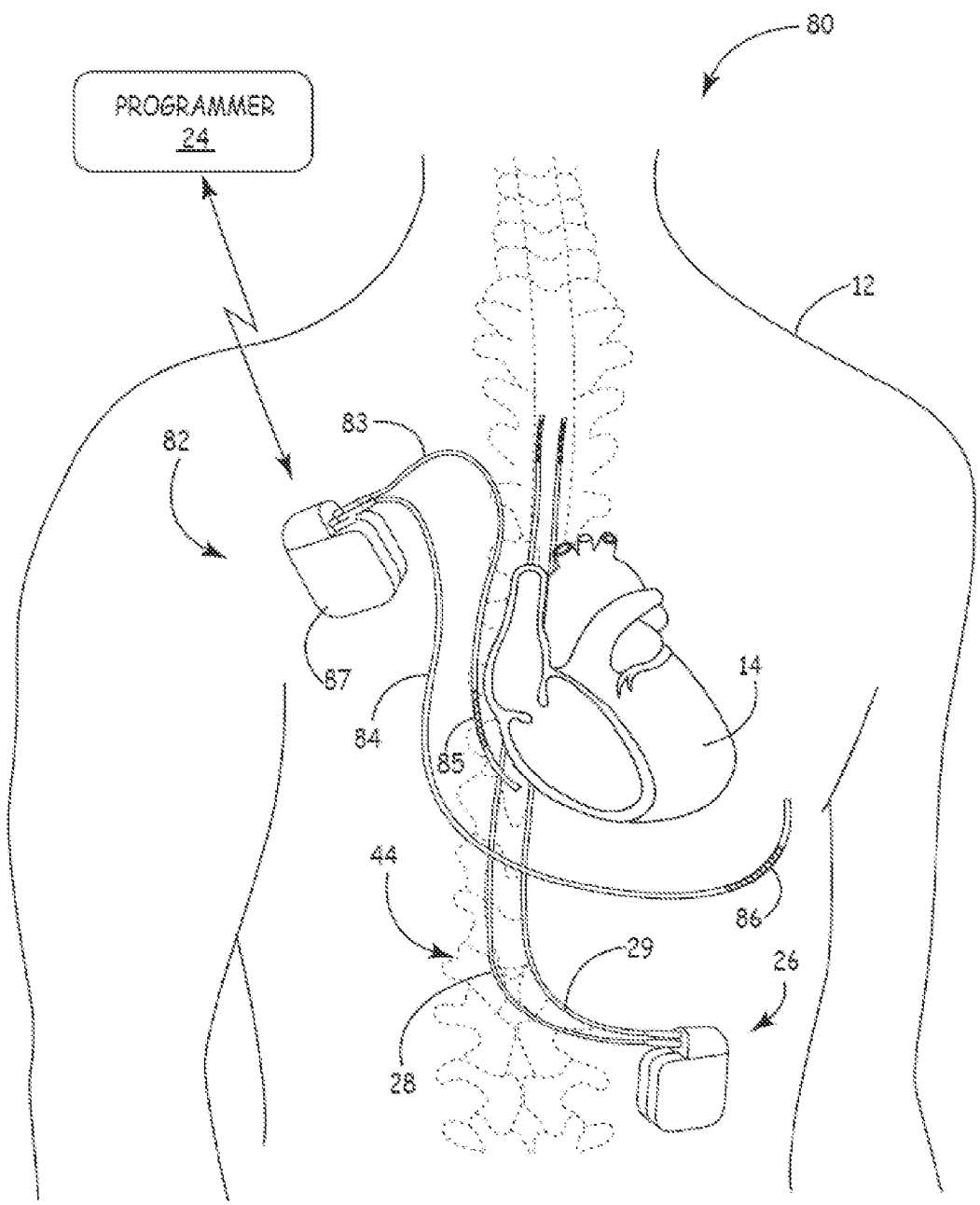
FIG. 5 is a conceptual diagram of another example therapy system that includes two medical devices to provide therapy to a patient.

FIG. 5 is a conceptual diagram of another example therapy system 80 that includes two medical devices to provide therapy to patient 12. In addition to INS 26 (lead 31 is not shown in FIG. 5), therapy system 80 includes ICD 82, which delivers electrical stimulation to heart 14 without intravascular leads. ICD 82 is coupled to extravascular leads 83, 84, which each include at least one electrode 85, 86, respectively. Electrodes 85, 86 may be subcutaneous coil electrodes, which may be positioned within a subcutaneous tissue layer of patient 12. In other examples, electrodes 85, 86 may comprise any other suitable type of extravascular electrode. For example, electrodes 85, 86 may include any other type of subcutaneous electrode, such as subcutaneous ring electrodes, subcutaneous plate electrodes, subcutaneous patch or pad electrodes, or any other type of electrode, such as a submuscular electrode, an epicardial electrode or an intramural electrode.

Electrodes 85 may be located within the thoracic cavity of patient 12 proximate to right ventricle 32 (FIG. 1), on the patient's side or back, or any other portion of the body appropriate for providing electrical stimulation to heart 14. Electrode 86 may be located within the thoracic cavity of patient 12 proximate left ventricle 36 (FIG. 1), on the patient's side or back, or any other portion of the body appropriate for providing electrical stimulation to the heart. Similar extravascular electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

Leads 83, 84 may be electrically coupled to stimulation modules, and, in some cases, sensing modules, that are enclosed within outer housing 87 of ICD 82. As with housing 70 of ICD 16 (FIG. 3), outer housing 87 may comprise a hermetic housing that substantially encloses the components of ICD 82, such as a sensing module, stimulation generator, processor and the like. Components of an example ICD 16 or ICD 82 are described with respect to FIG. 6. ICD 82 may deliver electrical stimulation (e.g., pacing, cardioversion or defibrillation pulses) to heart 14 between electrodes 85, 86 e.g., in a bipolar configuration. In other examples, ICD 82 may deliver electrical stimulation to heart 14 between electrodes 85 and housing 87 (or an electrode attached to an outer surface of housing 87), or between electrode 86 and housing 87, e.g., in a unipolar configuration.

While the disclosure primarily refers to therapy system 10 including ICD 16 (FIG. 1) and INS 26, the description of the techniques, systems, and devices herein are also applicable to therapy system 80 including ICD 82 and INS 26.

Figure 6:
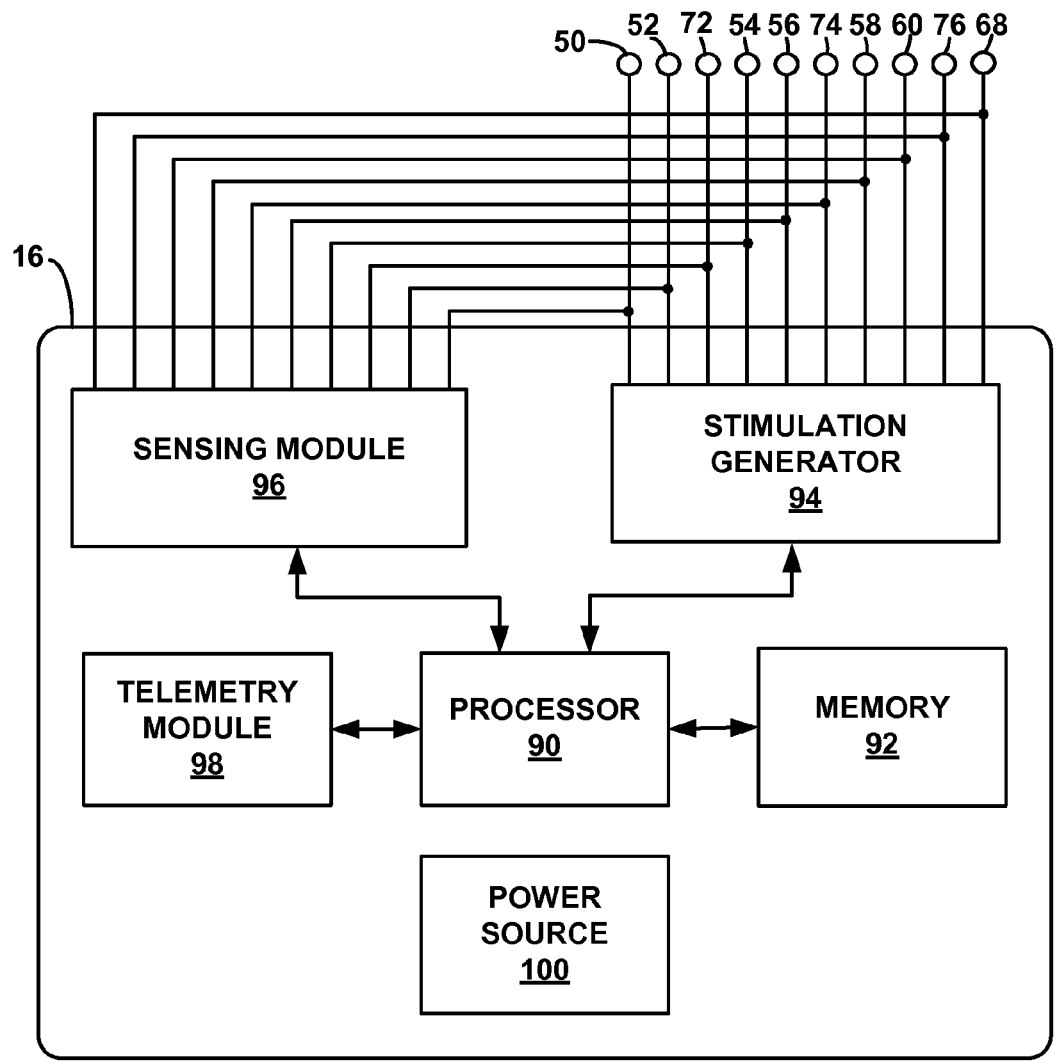
FIG. 6 is a functional block diagram of an example ICD that generates and delivers cardiac rhythm therapy to a heart of a patient.

FIG. 6 is a functional block diagram of an example configuration of ICD 16, which includes processor 90, memory 92, stimulation generator 94, sensing module 96, telemetry module 98, and power source 100. The block diagram shown in FIG. 6 may also illustrate an example configuration of ICD 82 (FIG. 5). Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls stimulation generator 94 to deliver stimulation therapy to heart 14 according to a selected one or more of therapy programs, which may be stored in memory 92. Specifically, processor 90 may control stimulation generator 94 to deliver electrical pulses with the amplitudes, pulse widths, frequency, or electrode polarities specified by the selected one or more therapy programs.

Stimulation generator 94 is electrically coupled to electrodes 50, 52, 54, 56, 58, 60, 68, 72, 74, and 76, e.g., via conductors of the respective lead 18, 20, 22, or, in the case of housing electrode 68, via an electrical conductor disposed within housing 70 of ICD 16. Stimulation generator 94 is configured to generate and deliver electrical stimulation therapy to heart 14 to manage rhythm of heart 14. For example, stimulation generator 94 may deliver defibrillation shocks to heart 14 via at least two electrodes 68, 72, 74, 76. Stimulation generator 94 may deliver pacing pulses via ring electrodes 50, 54, 58 coupled to leads 18, 20, and 22, respectively, helical electrodes 52, 56, and 60 of leads 18, 20, and 22, respectively, and/or housing electrode 68. In some examples, stimulation generator 94 delivers pacing, cardioversion or defibrillation therapy in the form of electrical pulses. In other examples, stimulation generator 94 may deliver one or more of these types of therapy in the form of other signals, such as sine waves, square waves, or other substantially continuous time signals.

In some examples, stimulation generator 94 may include a switch module and processor 90 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, however, stimulation generator 94 may independently deliver stimulation to electrodes 50, 52, 54, 56, 58, 60, 68, 72, 74, and 76 or selectively sense via one or more of electrodes 50, 52, 54, 56, 58, 60, 68, 72, 74, and 76 without a switch matrix.

Sensing module 96 monitors signals from at least one of electrodes 50, 52, 54, 56, 58, 60, 68, 72, 74, and 76 in order to monitor electrical activity of heart 14, e.g., via an EGM signal. Sensing module 96 may also include a switch module (not shown in FIG. 6) to select which of the available electrodes are used to sense the heart activity. In some examples, processor 90 may select the electrodes that function as sense electrodes via the switch module within sensing module 96, e.g., by providing signals via a data/address bus. In some examples, sensing module 96 includes one or more sensing channels, each of which may comprise an amplifier. In response to the signals from processor 90, the switch module of within sensing module 96 may couple the outputs from the selected electrodes to one of the sensing channels.

In some examples, sensing module 96 may include a plurality of channels. One channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, in one operating mode of sensing module 96, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, in one operating mode of sensing module 96, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an electrogram (EGM). In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

In some examples, sensing module 96 may monitor electrical activity of heart 14 via at least one of electrodes 50, 52, 54, 56, 58, 60, 68, 72, 74, and 76. The sensed electrical activity may be analyzed by processor 90 to determine if the electrical activity is consistent with that of heart 14 generating mechanical contractions. As described in further detail below, the sensed electrical activity may be evaluated in view of the one or more physiological parameters of patient 12 other than electrical cardiac activity to determine an EMD state of heart 14. For example, if the sensed electrical cardiac activity indicates heart 14 is in a sinus rhythm but the one or more sensed physiological parameters of patient 12 indicate heart 14 is not generating mechanical contractions or physiologically significant mechanical contractions, then either ICD 16, INS 26 or another device (e.g., programmer 24) may determine that heart 14 is in an EMD state. Upon determining heart 14 is in an EMD state, electrical stimulation therapy may be delivered to a tissue site of patient 12 to modulate afferent nerve activity and/or inhibit efferent activity. Such stimulation may help terminate the EMD state by, for example, increasing the contraction of cardiac muscle of heart 14. In other examples, INS 26 or a suitable sensing device, rather than ICD 16, may sense the electrical activity of heart 14, as described, to determine if heart 14 is in an EMD state.

Additionally or alternatively, the electrical activity of heart 14 monitored by sensing module 96 may be analyzed by processor 90 to determine autonomic nervous system activity associated with an EMD state of heart 14. If the sensed electrical activity reflects depressed or overexcited autonomic activity (e.g., sympathetic or parasympathetic nervous system activity) associated with an EMD state, then INS 26, ICD 16, or other device may deliver electrical stimulation to module autonomic activity of patient 12 based on the autonomic activity determined to be associated with the EMD state. For example, if processor 90 or a processor of INS 26 determines that the sensed electrical activity indicates overexcited sympathetic activity (e.g., based on a relatively high heart rate) just before or during the detection of an EMD state, then INS 26 can control the delivery of electrical stimulation therapy to a nonmyocardial tissue site or a nonvascular cardiac tissue site of patient 12 to decrease or depress sympathetic activity. Such stimulation may help terminate the EMD state and help address an underlying cause of the EMD state. In other examples, INS 26 or a suitable sensing device, rather than ICD 16, may sense the electrical activity of heart 14, as described, to determine autonomic nervous system activity associated with an EMD state.

If ICD 16 is configured to generate and deliver pacing pulses to heart 14, processor 90 may include a pacer timing and control module, which may be embodied as hardware, firmware, software, or any combination thereof. The pacer timing and control module may comprise a dedicated hardware circuit, such as an ASIC, separate from other processor 90 components, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. When a pacing code includes "D" as the third letter in the code, it may indicate that the sensed signal is used for tracking purposes.

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pacer timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

During pacing, escape interval counters within the pacer timing/control module of processor 90 may be reset upon sensing of R-waves and P-waves. Stimulation generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by stimulation generator 94, and thereby control the basic timing of cardiac pacing functions, including antitachyarrhythmia pacing.

The value of the count present in the escape interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, the count in the interval counters may not meet the requirements for triggering a therapeutic response.

In some examples, processor 90 may operate as an interrupt driven device, and is responsive to interrupts from the pacer timing and control module, where the interrupts may correspond to the occurrences of sensed P-waves and R-waves and the generation of cardiac pacing pulses. Any necessary mathematical calculations to be performed by processor 90 and any updating of the values or intervals controlled by the pacer timing and control module of processor 90 may take place following such interrupts. A portion of memory 92 may be configured as a plurality of recirculating buffers, capable of holding series of measured intervals, which may be analyzed by processor 90 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 90 in other examples.

In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 92 of ICD 16. In addition, the number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variability of the intervals between tachycardia events. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by stimulation generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, stimulation generator 94 may include a high voltage charge circuit and a high voltage output circuit. In the event that generation of a cardioversion or defibrillation pulse is required, processor 90 may employ the escape interval counter to control timing of such cardioversion and defibrillation pulses, as well as associated refractory periods. In response to the detection of atrial or ventricular fibrillation or tachyarrhythmia requiring a cardioversion pulse, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of stimulation generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging. Thereafter, timing of the delivery of the defibrillation or cardioversion pulse by stimulation generator 94 is controlled by the cardioversion/defibrillation control module of processor 90. Following delivery of the fibrillation or tachycardia therapy, processor 90 may return stimulation generator 94 to a cardiac pacing function and await the next successive interrupt due to pacing or the occurrence of a sensed atrial or ventricular depolarization.

Stimulation generator 94 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of stimulation generator 94.

Telemetry module 98 includes any suitable hardware, firmware, software or any combination thereof for communicating with another device, such as INS 26 or programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer.

In some examples, processor 90 may transmit atrial and ventricular heart signals (e.g., ECG signals) produced by atrial and ventricular sense amp circuits within sensing module 96 to programmer 24. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of ICD 16 are coupled to power source 100, which may include a rechargeable or non-rechargeable battery. A non-rechargeable battery may be selected to last for several years, while a rechargeable battery may be inductively charged from an external device, e.g., on a daily or weekly basis. Examples of a rechargeable battery include, but are not limited to, a lithium ion battery, a lithium polymer battery or a supercapacitor.

In some examples, data from sensing module 96 may be uploaded to a remote server, from which a clinician or another user may access the data to determine whether a potential sensing integrity issue exists. An example of a remote server includes the CareLink Network, available from Medtronic, Inc. of Minneapolis, Minn.

Figure 7:
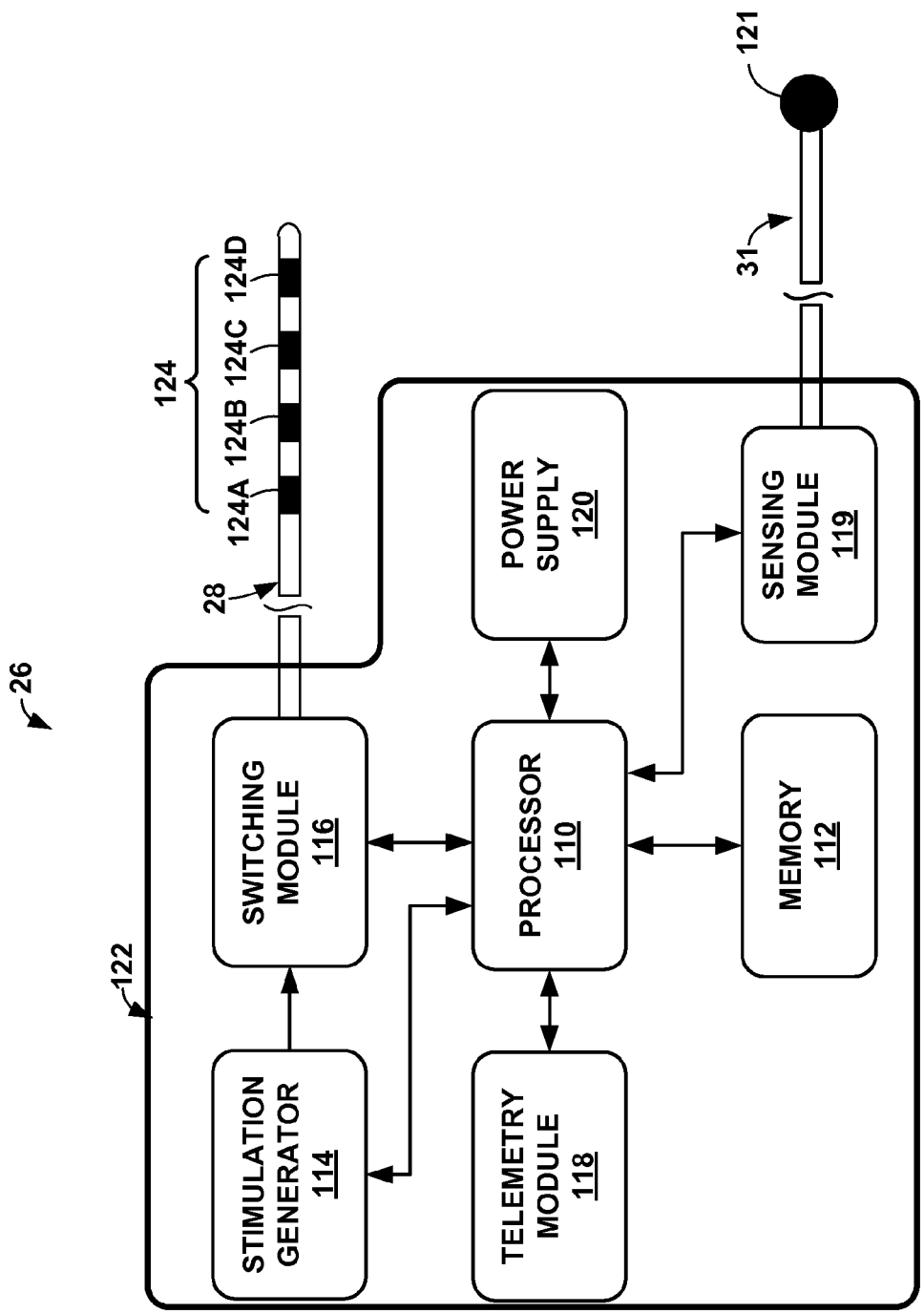
FIG. 7 is a functional block diagram of an example INS that generates and delivers electrical stimulation to a target tissue site of a patient.

Telemetry module 98 may also be useful for communicating with INS 26, which may also include a telemetry module as described with respect to FIG. 7. In some examples, INS 26 and ICD 16 may communicate with each other by way of RF communication techniques supported by the respective telemetry modules. In addition to or instead of the RF communication techniques, INS 26 and ICD 16 may communicate with each other by generating electrical communication signals that are sensed via the other device.

An example of a suitable communication technique for exchanging information between ICD 16 and INS 26 is described in commonly-assigned U.S. Pat. No. 4,987,897 to Funke, which is entitled, "BODY BUS MEDICAL DEVICE COMMUNICATION SYSTEM," and issued on Jan. 29, 1991 and is incorporated herein by reference in its entirety.

FIG. 7 is a functional block diagram of an example INS 26. INS 26 includes processor 110, memory 112, stimulation generator 114, switching module 116, telemetry module 118, sensing module 119, and power source 120. In the example shown in FIG. 7, processor 110, memory 112, stimulation generator 114, switching module 116, telemetry module 118, sensing module 119, and power source 120 are enclosed within outer housing 122, which may be, for example a hermetic housing. As shown in FIG. 7, stimulation generator 114 is coupled to lead 28 either directly or indirectly (e.g., via a lead extension). Alternatively, stimulation generator 114 may be coupled to more than one lead directly or indirectly (e.g., via a lead extension, such as a bifurcating lead extension that may electrically and mechanically couple to two leads) as needed to provide neurostimulation therapy to patient 12. Similarly, as shown in FIG. 7, sensing module 119 is coupled to lead 31 directly or indirectly (e.g., via a lead extension). Alternatively, sensing module 119 may be couple to more than one lead directly or indirectly as needed to sense one or more physiological parameters of patient that may be used to detect the EMD state of heart 14, as described herein. The physiological parameters may indicate whether heart 14 is providing sufficient cardiac output. The lack of sufficient cardiac output combined with an electrical cardiac signal that indicates heart 14 is in a sinus rhythm may indicate patient 12 is in an EMD state.

In the example illustrated in FIG. 7, lead 28 includes electrodes 124A-124D (collectively referred to as "electrodes 124"). Electrodes 124 may comprise ring electrodes. In other examples, electrodes 124 may be arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 124 illustrated in FIG. 7 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 124.

Memory 112 includes computer-readable instructions that, when executed by processor 110, cause INS 26 to perform various functions. Memory 112 may include any volatile, non-volatile, magnetic, optical, or electrical media, such as a RAM, ROM, NVRAM, EEPROM, flash memory, or any other digital media. Memory 112 may store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for measuring the impedance of electrodes 124.

Stimulation generator 114 generates stimulation signals, which may be pulses as primarily described herein, or continuous time signals, such as sine waves, for delivery to patient 12 via selected combinations of electrodes 124. Processor 110 controls stimulation generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Processor 110 may also control switching module 116 to apply the stimulation signals generated by stimulation generator 114 to selected combinations of electrodes 124. In particular, switching module 116 couples stimulation signals to selected conductors within leads 28 which, in turn, deliver the stimulation signals across selected electrodes 124. Switching module 116 may be a switch array, switch matrix, multiplexer, or any other type of switching device suitable to selectively couple stimulation energy to selected electrodes. Hence, stimulation generator 114 is coupled to electrodes 124 via switching module 116 and conductors within leads 28. In some examples, INS 26 does not include switching module 116.

Stimulation generator 114 may be a single or multi-channel stimulation generator. In particular, stimulation generator 114 may be capable of delivering a single stimulation pulse, multiple stimulation pulses, or a continuous signal at a given time via a single electrode combination or multiple stimulation pulses at a given time via multiple electrode combinations. In some examples, however, stimulation generator 114 and switching module 116 are configured to deliver multiple channels on a time-interleaved basis. In this case, switching module 116 serves to time division multiplex the output of stimulation generator 114 across different electrode combinations at different times to deliver multiple programs or channels of stimulation energy to patient 12.

Sensing module 119 may sense one or more physiological parameters of patient 12 via sensor 121 of lead 31. As described in greater detail below, the one or more physiological parameters of patient 12 sensed by sensing module 119 may include physiological parameters appropriate for determining if heart 14 is in an EMD state. For example, sensor module 119 may be configured to sense one or more physiological parameters indicative of mechanical contraction of heart 14 via sensor 121. In some examples, sensing module 119 senses one or more of blood pressure and blood flow via sensor 121. Blood flow and blood pressure may change as a function of mechanical contraction of heart 14. A blood pressure or blood flow through heart 14 or other vasculature (e.g., blood vessels or arteries) that falls below a particular threshold or decreases by a particular rate may indicate that heart 14 is not sufficiently contracting.

Other physiological parameters indicative of mechanical contraction of heart 14 includes tissue perfusion or blood oxygen saturation. Tissue perfusion and blood oxygen saturation may be sensed using any suitable technique, such as an optical perfusion sensor, a pulse oximeter, or a blood pressure pulse (e.g., a palpitation) detector. A pulse or palpitation detector can be, for example, by a sensor that detects rapid changes in perfusion that occur during a normal heart beat cycle, such as, e.g., an optical perfusion sensor, or a pressure or strain gauge sensor that detects blood vessel dilation/contraction. An optical perfusion sensor may detect general perfusion state associated with adequate heart function or inadequate heart function, or the optical perfusion sensor may detect relatively rapid changes in tissue perfusion that occur during a heartbeat that is pulsatile, thereby indicating some level of mechanical contraction of heart 14 is present. In some examples, an optical perfusion sensor, pulse oximeter, or blood pressure pulse detector may be positioned at a remote location from that of heart 14 and/or may be located at or adjacent to the housing of an IMD, such as, e.g., the housing of IMD 16 or IMD 26.

Example systems and techniques for monitoring tissue perfusion may include those described in U.S. patent application Ser. No. 11/963,045, entitled "OPTICAL SENSOR AND METHOD FOR DETECTING A PATIENT CONDITION," and filed Dec. 21, 2007, the entire content of which is incorporated herein by reference. As described, in some examples, tissue perfussion may be monitored using a light source emitting a light signal and light detector receiving emitted light scattered by the volume of body tissue. The light dector emits a signal having an alternating current (AC) component corresponding to the pulsatility of blood flow in the body tissue volume. In response to the AC component of the light detector signal, a processor may determine a patient condition (e.g., a heart rhythm). In some examples, a pulsatility metric may be to detected heart rate of a patient. The heart rate detected by the pulsatility metric may be compared to a heart rate determined based on monitored electrical signals (e.g., ECG) of a heart to confirm the heart rate indicated by the electrical signals. Using such a technique, tissue perfusion and/or pulsatility may be monitored to detect an EMD state of heart 14, e.g., an EMD state may be detected when the rate indicated by the pulsatility is consistent with lack of physiological significant mechanical contractions of heart 14 but the electrical activity of heart 14, e.g., ECG/EEG signals, during approximately the same time period is indicative of mechanical contraction of heart 14.

Various hemodynamic characteristics may be derived from relative changes in a blood oxygen saturation level or tissue perfusion of a patient, such as, e.g., relative changes in the blood pressure of the patient or the relative blood flow through a particular blood mass (e.g., a blood vessel or other vasculature), the presence of an acceptable blood flow pulse and/or the presence of palpitation. Therefore, blood oxygen saturation levels may be useful for determining whether heart 14 is contracting in a physiologically significant manner.

Additionally, in some examples, sensing module 119 senses electrical activity of heart 14 via sensor 121. Accordingly, sensor 121 may be any suitable type sensor capable of sensing the desired physiological parameter. In some examples, sensor 121 communicates parameter information to sensing module 119 via a wired connection, e.g., via lead 31. Alternatively, sensor 121 may communicate sensed parameter information to sensing module via a wireless connection, in which case sensor 121 may be physically separate from housing 122 and lead 31 may be eliminated from the therapy system. Sensing module 119 may communicate sensed physiological parameter information to processor 110, which may analyze the parameter information to determine if heart 14 is in an EMD state.

Sensing module 119 may also sense electrical activity of heart 14 and/or one or more nerves of patient 12. The sensed electrical activity may be used by processor 110 or other processor to evaluate autonomic nervous system activity, e.g., autonomic nervous system activity associated with an EMD state. Therapy delivered to patient 12 to treat an EMD state may be configured based on the autonomic activity associated with the EMD state. In general, as will be described further below, the delivered therapy may be configured to modulate autonomic activity in a manner determined to be appropriate (e.g., by processor 90 or processor 110) in view of the autonomic nervous system activity determined to be associated with an EMD state.

Telemetry module 118 supports wireless communication between INS 26 and ICD 16, as well as between INS 26 and an external programmer 24 (FIG. 1) or another computing device under the control of processor 110. Telemetry module 118 may also support wireless communication between sensing module 119 of INS 26 and sensor 121 in examples in which sensor 121 is physically separate from INS 26. Processor 110 of INS 26 may receive, as updates to programs, values for various stimulation parameters such as amplitude and electrode combination, from programmer 24 via telemetry module 118. The updates to the therapy programs may be stored within memory 112.

In some examples, processor 110 may store information associated with the detection and/or treatment of an EMD state for patient 14 in memory 112. Processor 110 may transmit information associated with the detection and/or treatment with external programmer 24 or other external device via telemetry module 118. In some examples, processor 110 may communicate with external programmer 24 when an EMD state to alert programmer 24 to the detection, which may then alert a user to the EMD state. In some examples, such communication may occur at or near real-time with the detection of the EMD state or may occur at some later time. Processor 110 may alternatively or additionally communicate whether or not the EMD state has been terminated. In some examples, processor 110 may communicate to external programmer 24 the type of stimulation therapy (e.g., one or more therapy programs) used to treat the EMD state as well as an identification of which stimulation therapy was effective in terminating the EMD state. EGM signals or other electrical activity of heart 14 of patient 12 that is associated with the EMD state and/or response to treatment may also be communicated to programmer 24. In this manner, programmer 24 may allow a user to be alerted to the occurrence of an EMD state, e.g., as it occurs, to be able to observe how the INS 26 responded to the EMD state, and/or observe the response of patient 12 to the situation.

The various components of INS 26 are coupled to power supply 120, which may include a rechargeable or non-rechargeable battery. A non-rechargeable battery may be selected to last for several years, while a rechargeable battery may be inductively charged from an external device, e.g., on a daily or weekly basis. In other examples, power supply 120 may be powered by proximal inductive interaction with an external power supply carried by patient 12.

Figure 8:
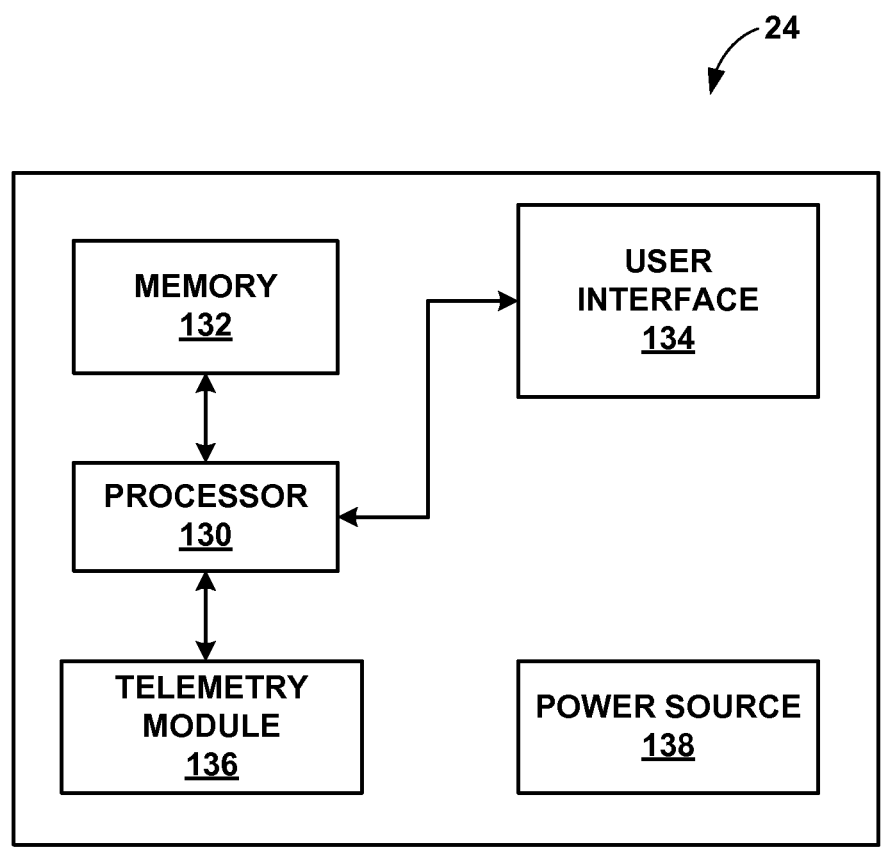
FIG. 8 is a functional block diagram of an example medical device programmer.

FIG. 8 is block diagram of an example programmer 24. As shown in FIG. 6, programmer 24 includes processor 130, memory 132, user interface 134, telemetry module 136, and power source 138. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The clinician may interact with programmer 24 via user interface 134, which may include display to present graphical user interface to a user, and a keypad or another mechanism for receiving input from a user.

Processor 130 can take the form one or more microprocessors, DSPs, ASICs, FPGAs, programmable logic circuitry, or the like, and the functions attributed to processor 130 herein may be embodied as hardware, firmware, software or any combination thereof. Memory 132 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed over heart 14, as described above with reference to FIG. 1. Telemetry module 136 may be similar to telemetry module 98 of ICD 16 (FIG. 6) or telemetry module 118 of INS 26 (FIG. 7).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

Figure 9:
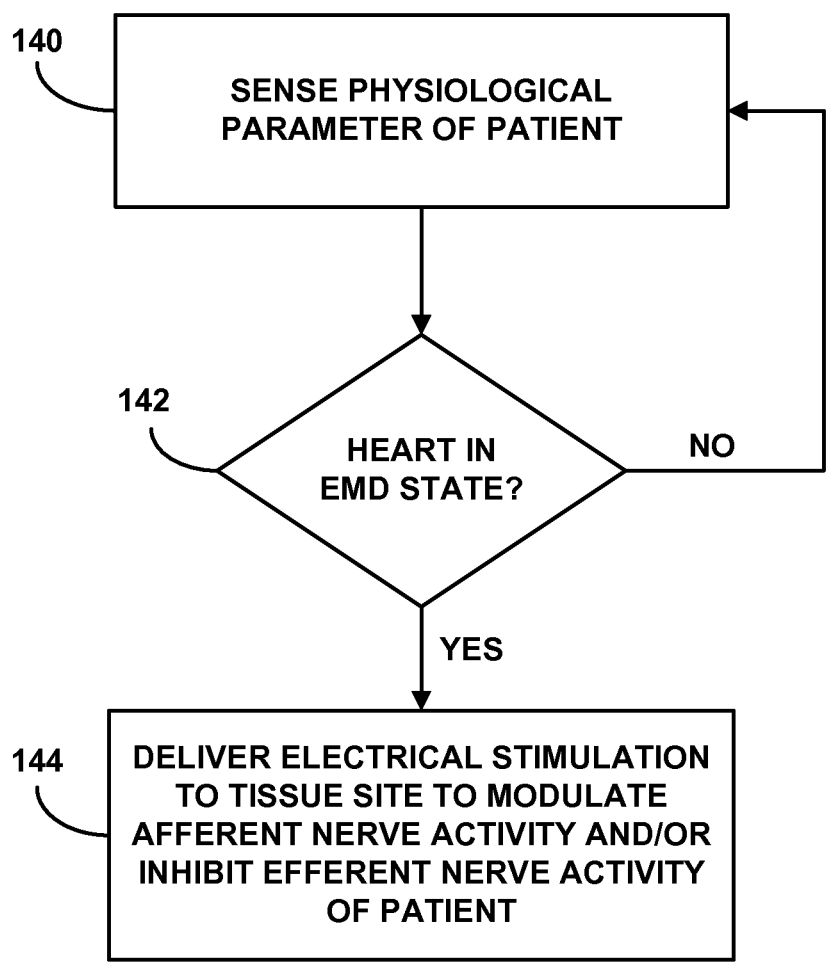
FIG. 9 is a flow diagram illustrating an example technique for determining when a heart of a patient is in an EMD state and delivering electrical stimulation to a patient upon determining the heart is in the EMD state.

FIG. 9 is a flow diagram illustrating an example technique for delivering electrical stimulation to a patient 12 when heart 14 is in an EMD state. For purposes of illustration, the example techniques of FIGS. 9-14 are described with respect to patient 12 and therapy system 10 of FIG. 2. However, examples are not limited to such a configuration of therapy system 10, but instead may be applied to any system or device, e.g., a system or device that is configured to determine that heart 14 is in an EMD state based on one or more sensed physiological signals, and deliver electrical stimulation to any appropriate tissue site to modulate afferent nerve activity and/or inhibit efferent nerve activity when it is determined that heart 14 of patient 12 is in an EMD state, as described herein.

As indicated by FIG. 9, in some examples, INS 26 senses at least one physiological parameter of patient 12 (140), e.g., via sensor 121 (FIG. 7) of lead 31. Based at least in part on the one or more sensed physiological parameters, processor 110 of INS 26 may determine whether heart 14 is in an EMD state (142). For example, INS 26 may determine that that heart 14 is in an EMD state if a sensed physiological parameter other than that of the electrical activity of heart 14, e.g., blood pressure and/or blood flow, is indicative of the absence of physiologically significant mechanical contractions of heart 14 but the electrical activity of heart 14, e.g., ECG/EEG signals, during approximately the same time period is indicative of mechanical contraction of heart 14. Such an example is further described with respect to FIG. 10 below.

If processor 110 determines that heart 14 is in an EMD state, processor 110 may control stimulation generator 114 to deliver electrical stimulation to a tissue site of patient 12 via selected electrodes 124 of lead 28 in order to modulate afferent nerve activity and/or inhibit efferent nerve activity (144). The electrical stimulation delivered by INS 26 may be delivered in manner that results in mechanical contraction of heart 14 to terminate of the EMD state of heart 14. On the other hand, if processor 110 determines that heart 14 is not in an EMD state, processor 110 may continue monitoring one or more physiological parameters of patient (140), which may be indicative of both electrical cardiac activity and mechanical activity of heart 14.

As previously described, an EMD state may be a condition characterized by the persistence of electrical activity in the heart without associated mechanical contraction or with a relatively low level of mechanical contraction. Accordingly, in some examples, the one or more physiological parameters sensed by INS 26 via sensor 121 may be physiological parameters indicative of the mechanical contraction, or lack thereof, of heart 14, and sensor 121 may be any suitable type sensor capable of sensing such a desired physiological parameter.

In some examples, physiological parameters that are indicative of mechanical contraction of heart 14 include one or more of blood pressure, blood oxygen saturation level, movement of heart muscles, and blood flow, which may include arterial blood flow, venous blood flow and/or and blood flow in tissue (e.g., tissue perfusion). INS 26 may sense these physiological parameters of patient 12 via sensor 121. In some examples, sensor 121 includes one or more pressure sensors configured to monitor the blood pressure of patient 12, e.g., by monitoring pressure within right ventricle 32 or left ventricle 36 (FIG. 1). As other examples, sensor 121 may include one or more of flow meters, Doppler flow sensors, MRI imaging sensors such as those sensors configured for echo planar imaging (EPI), ion transport sensors, oxygen sensors, pH sensors, blood calcium sensors, blood sugar sensors, piezoelectric sensors, accelerometers, microphones, stress sensors, bend sensors, tissue perfusion sensors and acoustic sensors. Sensor 121 may be located inside heart 14, on the outer surface of heart 14, adjacent to heart 14, and/or other suitable location on or implanted within the body of patient 12.

Flow meters and/or Doppler flow sensors may monitor arterial and/or venous blood flow rates, which are directly influenced by mechanical contractions of heart 14. Doppler sensors may also be utilized to measure heart motion to detect insufficient or inappropriate or ineffective heart motion, which can indicate the failure of heart 14 to sufficiently contract. In a similar manner, an ion transport sensor may monitor blood flow by monitoring the flow of ions contained in the blood of patient 12, e.g., mineral ions. As another example, one or more oxygen sensors may be used to monitor oxygen levels in the blood of patient 12 as an indicator of mechanical contraction of heart 14. Generally, blood oxygen saturation levels may increase with contraction of the heart because, as the volume of blood that is output by heart 14 increases, the blood oxygen saturation level typically increases.

In a similar manner, one or more sensors that monitor pH of a patient's blood may be used since the concentration of hydrogen ions in blood of a patient may be correlated with mechanical contraction of heart 14. For example, a reduction in blood flow may result in a reduction of the pH of the patient's blood. In some examples, a pH sensor may detect acidosis or relatively low pH, which can be at least a part of the reason for the EMD state has occurred or persists. Thus, in some examples, measured pH of a patient's blood may be used to detect an EMD state or confirm an EMD state detected, for example, via another sensed physiological parameter.

Blood calcium sensors may be used, e.g., to detect blood calcium concentrations for patient 12. If sufficient calcium is not available, cardiac contractility may suffer and contribute to EMD. Thus, in some examples, measured blood calcium concentration may be used to detect an EMD state or confirm an EMD state detected, for example, via another sensed physiological parameter. Similarly, blood sugar sensors may be used, e.g., to detect blood sugar levels for patient 12. The presence of hypoglycemia may contribute to an EMD state. Thus, in some examples, measured blood sugar levels may be used to detect an EMD state or confirm an EMD state detected, for example, via another sensed physiological parameter.

Piezoelectric sensors may be used, e.g., to detect blood pressure and/or acceleration associated with pulses through patient 12 (e.g., through a blood mass, such as a blood vessel or artery), both of which may be an indicator of mechanical contraction of heart 14. Acoustic sensors may also be used by monitoring acoustic signal or sounds generated with blood flow, which is influenced by the mechanical contraction of heart 14, or to monitor acoustic signal or sounds of one or more contractions of heart 14.

Furthermore, sensor 121 may be positioned relative to patient 12 to allow INS 26 to monitor the selected physiological parameters. In some examples, sensor 121 may be capable of directly sensing the mechanical contraction of heart 14 by sensing the movement of heart 14 corresponding to mechanical contractions of heart 14, e.g., via one or more single or multi-axis accelerometers positioned in cardiac tissue of heart 14 or tissue proximate to heart 14. As another example, one or more accelerometers or other sensors may be location proximate or within blood vessel(s) that are directly connected to heart 14, such as larger blood vessels such as the pulmonary vein, pulmonary artery, vena cava, aorta, and the like, to detect mechanical contractions of the heart. In some examples, ultrasonic imaging sensors may also be used to provide ultrasonic images of heart 14 that may be used to determine if heart 14 is contracting in a physiological significant manner. An accelerometer or ultrasonic signal may be used to detect an EMD state, for example, using a baseline signal template captured when heart 12 was operating in a non-EMD state, that is subsequently compared to one or more measured signals to determine if the measured signals are consistent with the baseline template. If not consistent with the baseline template, the signals may indicate that an EMD state may be present.

In some examples, electrical activity of heart 14 may be monitored by INS 26 to determine if heart 14 is in an EMD state. For example, sensor 121 coupled to INS 26 may include one or more sense electrodes configured to monitor electrical signals of heart 14, in conjunction with the one or more physiological parameters indicative of mechanical contraction previously described, in a manner that may be used to determine if heart 14 is in an EMD state. Alternatively, or additionally, in some examples, the electrical activity of heart 14 may be monitored via electrodes on one or more of leads 18, 20, 22 coupled to ICD 16, which may monitor the same or similar electrical activity of heart 14 to properly deliver of at least one of pacing, cardioversion, or defibrillation therapy to heart 14 of patient 12. In such examples, ICD 16 may communicate information regarding the sensed electrical activity of heart 14 to INS 26, e.g., via the respective telemetry modules 98 and 118, so that INS 26 may determine whether heart 14 is in an EMD state. As will be described below, the electrical activity of heart sensed by INS 26 and/or ICD 16 may be analyzed in conjunction with the corresponding physiological parameters to determine whether or not heart 14 is exhibiting normal electrical activity, at least to the extent that the electrical activity may be typical to that of a heart in an EMD state 14.

In one example, INS 26 may monitor the peak endocardial interval (PEI) using sensor 121 to determine whether heart 14 is in an EMD state. The PEI may be characterized as the time between the peak of an electrical signal of heart 14 (e.g., such as the Q peak of the QRS complex) and the peak magnitude of the acceleration of heart 14, e.g., as measure by an accelerometer sensor. In general, the PEI interval normally is about 150 milliseconds to about 250 milliseconds after the Q peak of the QRS complex for a heart that is contracting in a physiologically significant manner. In cases in which heart 14 is in an EMD state, the PEI interval may be outside the normal PEI interval, for example, due to the failure of heart to mechanically contract, thereby increasing the PEI interval.

In some examples, INS 26 (or other device) may monitor the respiration of patient 12 to determine whether heart 14 is in an EMD state. Hypoxia secondary to respiratory failure may be a cause of an EMD state, and respiratory insufficiency can be present during the occurrence of an EMD state. Accordingly, INS 26 may be configured to monitor for instances of respiratory insufficiency, acute respiratory arrest or other respiratory condition associated with EMD to at least in part detect when heart 14 is in an EMD state. In some example, respiratory insufficiency and/or acute respiratory arrest may be used to confirm the identification of an EMD state based on one or more other physiological parameters.

INS 26 and/or ICD 16 may monitor respiration parameters, such as the rate profile of inhalation and/or exhalation and the respiration rate, by sensing thoracic impedance to determine if patient 12 is breathing normally or abnormally. Normal breathing or abnormal breathing can be indicated by, for example, a threshold respiration rate or a threshold range of respiration rates, or by a template that indicates a profile of inhalation and exhalation patterns that is normal or abnormal (e.g., indicative of the possible presence of an EMD state). In some examples, INS 26 may control stimulation generator 114 (FIG. 7) to deliver stimulation to patient 12 to treat an EMD state if patient 12 is breathing abnormally. In some example, INS 26 may apply the electrical stimulation to treat EMD if patient is breathing abnormally in conjunction with the determination that another physiological parameter of patient is indicative of heart 14 being in an EMD state.

Processor 110 or other processor of another device may analyze sensed physiological parameter information to determine whether heart 14 is in an EMD state. For example, processor 110 may analyze the sensed physiological parameter information using one or more suitable algorithms configured to detect an EMD state based on sensed parameter information. In some examples, a detection algorithm may weight one or more patient factors that may increase or decrease the overall likelihood of heart 14 of patient 12 being in an EMD state. Such patient factors may include the age and/or gender of patient 12. For example, the algorithm can reflect the possibility that heart 14 may be more likely to enter an EMD state in cases in which patient 12 is a female. As another example, the algorithm can increase the possibility that a particular physiological parameter indicates heart 14 is in an EMD state based on the age of patient 12; heart 14 may be more likely to enter an EMD state with increased age of patient 12. For example, EMD of heart 14 may by more likely to occur in a patient that is older than, e.g., seventy years of age compared to that of patient 12 that is younger than seventy years of age.

Accordingly, the detection algorithm applied by processor 110 (e.g., by executing one or more machine readable instructions stored in memory 112 of INS 26) may incorporate patient factors of patient 12 that may increase or decrease the likelihood of heart 14 entering an EMD state. Such factors may be taken into account, for example, in cases in which sensed physiological parameter and other information analyzed by processor 110 indicate a borderline determination of an EMD state of patient, e.g., a determination that there is a small probability that a particular physiological parameter indicates the EMD state is occurring. For example, if a borderline EMD state determination is made and one or more patient factors, such as age or sex, reflect an increased likelihood of heart 14 entering an EMD state, then processor 110 may determine that heart 14 is in an EMD state. Conversely, if a borderline EMD state determination is made and one or more patient factors, such as age or sex, do not reflect an increased likelihood of heart 14 entering an EMD state, then processor 110 may determine that heart 14 is not in an EMD state. A clinician can adjust the EMD state detection algorithm according to the factors known to the clinician to better indicate whether a particular physiological parameter indicates heart 14 of patient 12 is in an EMD state.

Although sensor 121 is shown to be positioned within or proximate to heart 14 of patient 12 in the examples of FIGS. 1 and 2, in other examples, sensor 121 may have any suitable position relative to heart 14. Sensor 121 may positioned at any suitable location with respect to patient 12 that allows sensor 121 to properly monitor one or more desired physiological parameters that are indicative of mechanical contraction of heart 14. Furthermore, in some examples, sensor 121 is implanted within patient 12, e.g., as shown in the examples of FIGS. 1 and 2. In other examples, sensor 121 is located external to patient 12 in a position that allows sensor 121 to monitor the desired physiological parameter. As one example, a sensor 121 that monitors the pulse of patient 12 may be incorporated into a wristband that may be worn on the wrist of patient 12, e.g., in the same manner as a wrist watch.

INS 26 may deliver electrical stimulation to modulate afferent nerve activity of patient 12 by configuring the electrical stimulation to modify the afferent nerve activity of patient 12. For example, stimulation generator 114 (FIG. 7) of INS 26 may deliver electrical stimulation that is configured to excite an afferent nerve activity of a nerve of patient 12 and/or inhibit afferent nerve activity. In general, afferent nerve activity includes nerve impulses sent from receptors or sense organs to the central nervous system, e.g., the brain and spinal cord, via afferent nerve pathways. Such nerve impulses may be associated with the sensory function of the nervous system patient by providing information to the central nervous system brain gathered via the peripheral nervous system.

By modulating afferent nerve activity via delivery of electrical stimulation when it is determined that patient 12 is in an EMD state, the EMD state may be treated without delivering electrical stimulation that directly excites efferent nerve activity within efferent nerve pathways associated with heart 14 of patient 12. Instead, the EMD state may be treated by directly modulating the nerve impulses that are sent to the brain of patient 12 via electrical stimulation rather than those sent from the brain. In turn, depending on the nature of the afferent nerve activity modulation, the patient's brain may react to the modulated afferent nerve activity in a manner that treats (e.g., helps terminate) the EMD state of the heart, e.g., by causing sufficient mechanical contraction of heart 14. Treating an EMD state of heart 14 may include, for example, increasing the mechanical contraction of heart 14.

In some examples, delivery of electrical stimulation to inhibit afferent nerve activity may act to prevent the delivery of certain impulses to the brain of patient 12 via afferent pathways. In the absence of such afferent nerve impulse, the brain may react in a manner that helps treat the EMD state. For example, in the absence of such impulses, the brain may react by sending one or more impulses to heart 14 via efferent nerve pathways in a manner that results in the increased mechanical contraction of heart 14.

Furthermore, in some examples, delivery of electrical stimulation by INS 26 to excite afferent nerve activity of patient 12 may promote the delivery of certain impulses to the brain via afferent pathways. In the presence of such afferent nerve impulses, the brain of patient 12 may react in a manner that effectively treats the EMD state. For example, in the presence of such impulses, the brain may again react by sending one or more impulses to heart 14 via efferent nerve pathways in a manner that results in the increased mechanical contraction of heart 14.

Alternatively, or in addition to the modulation of afferent nerve activity, the electrical stimulation may be delivered to patient 12 to inhibit efferent nerve activity when it is determined that heart 14 of patient 12 is in an EMD state. Efferent nerve activity includes nerve impulses sent from the central nervous system to effectors, e.g., muscles or glands, via efferent nerve pathways. Such nerve impulses may be associated with the motor function of patient 12, including muscular control, by providing a mechanism for the brain to communicate with the effectors.

By inhibiting efferent nerve activity via delivery of electrical stimulation when it is determined that patient 12 is in an EMD state, the EMD state may be treated without delivering electrical stimulation that directly excites efferent nerve activity within efferent nerve pathways associated with heart 14 of patient 12. Instead, the EMD state of heart 14 may be treated by directly inhibiting nerve impulses that have been sent from the brain of patient 12, or central nervous system in general, via efferent pathways to heart 14. In turn, the inhibition of the efferent nerve activity from the electrical stimulation may result in mechanical contraction of heart 14 to effectively treat the detected EMD state.

INS 26, via electrodes of lead 28, may deliver electrical stimulation to one or more tissue sites that allow for the modulation of afferent nerve activity and/or inhibition of efferent nerve activity, as described above. For example, INS 26 and lead 28 may deliver electrical stimulation to a nonmyocardial tissue site and/or a nonvascular cardiac tissue site to modulate afferent nerve activity and/or inhibit efferent nerve activity. In some examples, INS 26 and lead 28 may deliver electrical stimulation to one or more tissue sites proximate one or more afferent nerves or nerve bundles, e.g., in examples in which the delivery of electrical stimulation modulates afferent nerve activity. In other examples, INS 26 and lead 28 may deliver electrical stimulation to one or more tissue sites proximate one or more efferent nerves or nerve bundles, e.g., in examples in which the delivery of electrical stimulation inhibits efferent nerve activity. In still other examples, electrical stimulation may be delivered to the median nerve, vagal nerve, cardiac sympathetic nerve, and/or subcutaneous tissue that contains nerve fibers/sensors in order to modulate afferent nerve activity and/or inhibit efferent nerve activity.

In some examples, the tissue site of patient 12 to which INS 26 delivers the electrical stimulation when the EMD state of heart 14 is detected is a tissue site other than myocardial tissue of heart 14. Myocardial tissue of heart 14 may be the target tissue of pacing, cardioversion, and/or defibrillation therapy delivered by ICD 16. Accordingly, in some examples, INS 26 does not deliver electrical stimulation directly to tissue of heart 14. Despite the fact that the electrical stimulation is not delivered directly to a myocardial tissue site of heart, or even a noncardiac tissue site in general, the electrical stimulation delivered by INS 26 may help treat the EMD state of heart 14 by increasing the contraction of heart 14 such that the contraction of heart 14 and electrical cardiac signals are appropriately synchronized). In this manner, INS 26 may be utilized to treat an EMD state of heart 14.

In some examples, electrodes 124 of lead 28 may be positioned to deliver electrical stimulation to one or more sites proximate to spinal cord 44 (FIG. 2). For example, INS 26 may deliver electrical stimulation via lead 28 proximate to one or more vertebrae of patient 12. As another example, electrical stimulation may be delivered to a site proximate to one or more of thoracic segments, including thoracic segments T1-T6. For example, electrical stimulation may be delivered proximate to one or more of thoracic segments T3, T4, T5 and/or T6, including across one or more of the spans from T3 to T6, T4 to T6, and T1 to T6. In other examples, INS may deliver electrical stimulation via lead 28 to peripheral nerve locations in communication with spinal cord 44. By delivering electrical stimulation to one more of the above locations, afferent nerve activity may be modulated and/or efferent nerve activity may be inhibited in a manner that results in one or more mechanical contractions of heart 14 when in an EMD state.

INS 26 may generate and deliver electrical stimulation according to one or more therapy programs stored in memory 112 (FIG. 7) that define one or more parameters of appropriate electrical stimulation. In some examples, the pulse rate of the electrical stimulation signals delivered to patient 12 to treat the EMD state of the patient may range from approximately 1 Hz to approximately 200 Hz, such as, e.g., approximately 10 Hz to approximately 1 kilohertz. Additionally, example electrical stimulation signals may have a voltage ranging from approximately 0.2 volts to approximately 12 volts, such as, e.g., approximately 0.5 volts to approximately 10 volts. Example pulse width of the electrical stimulation signals may range from approximately 0.1 milliseconds to approximately 5 milliseconds, such as, e.g., 0.2 milliseconds. Other stimulation parameter values are contemplated.

In general, INS 26 may generate and deliver electrical stimulation the tissue site of patient 12 for a duration of time that is appropriate for terminating an EMD state of heart 14. The duration of time for delivery of electrical stimulation by INS 26 may less than the amount of time for the EMD state to be harmful to patient 12. In some examples, INS 26 is configured to generate and deliver electrical stimulation to the tissue site within a minimal amount of time after INS 26 has successfully determined that heart 14 is in an EMD state. For example, INS 26 may be configured to deliver electrical stimulation to the tissue site substantially immediately after INS 26 has successfully determined that heart 14 is in an EMD state. In some examples, INS 26 may be configured to delivery electrical stimulation to the tissue site of patient 12 between approximately 1 second to approximately 30 minutes after determining that heart 14 is in an EMD state.

In some examples, INS 26 may be configured to both determine heart 14 is in an EMD state and deliver electrical stimulation to the tissue site of patient 12, as previously described, within approximately 1 millisecond to approximately 30 seconds, such as, e.g., approximately 30 milliseconds to approximately 30 seconds, of heart 14 entering an EMD state. As will be described in greater details below with respect to FIG. 12, heart 14 may enter an EMD state after the delivery of cardioversion or defibrillation therapy to heart 14 via ICD 26. In such cases, INS 16 may determine if heart 14 is in an EMD state and deliver stimulation to the tissue site of patient 12, as previously described, within approximately 1 second to approximately 30 seconds, such as, e.g., approximately 5 second to approximately 30 seconds, of ICD 26 delivering cardioversion or defibrillation therapy.

In the event that the initial therapy delivered to patient 12 from INS 26 does not result in resolution of the EMD state, then processor 110 (FIG. 7) may be configured to sequentially run through a series of therapy programs, e.g., defining different stimulation signals, electrode combinations, and electrode locations, in an attempt to identify a therapy that is effective in terminating the EMD state of heart 14 and/or a more efficacious therapy for treating EMD. In some examples, INS 26 may deliver stimulation according to each program for between approximately 5 seconds to approximately 60 seconds. If a therapy is found to be effective in terminating the EMD state, INS 26 may continue with that therapy program until the EMD state is fully mitigated (e.g., heart 14 begins mechanically contracting in a physiologically significant manner) or may continue the therapy beyond initial mitigation. In some examples, INS 26 may continue to delivery therapy to patient 12 for approximately 30 seconds to approximately 120 minutes after the EMD state has been terminated as a follow-up therapy to help assure that EMD state does not imminently reappear. The stimulation therapy delivered by INS 26 can initiate at a relatively large amplitude or duty cycle "on" time to treat an EMD state. Then, after EMD is resolved, the stimulation therapy may be adjusted, e.g., to remain at a lower amplitude and/or duty cycle. In other examples, however, after a detected EMD state is addressed and INS 26 determines that heart 14 is mechanically contracting in a physiologically significant manner (e.g., using techniques described above or by receiving an indication from INS 26), INS 26 may discontinue all therapy delivery to patient 12 until another EMD state is detected.

In some examples, INS 26 may delivery therapy to patient 12 on a continuous or periodic basis to treat one or more other patient conditions. As such, INS 26 in not limited to delivery of stimulation to patient 12 upon the detection of an EMD state. In some examples, the stimulation therapy may include stimulation that modulates afferent nerve activity or inhibits efferent nerve activity, even in cases in which an EMD state is not detected. Stimulation therapy may be delivered to patient alternately between low intensity/duty cycle and high intensity/duty cycle, as a means to avoid habituation and reduction in therapeutic efficacy. In these examples, INS 26 can adjust the timing of therapy delivery, one or more stimulation parameter values or the target therapy delivery site based on the detection of an EMD state. The EMD therapy can be delivered in conjunction with or instead of the other therapy delivered by INS 26 to manage other patient conditions.

As described below, in some examples, INS 26 delivers stimulation to treat an EMD state in conjunction with the delivery of a cardioversion or defibrillation signal from ICD 12. The EMD stimulation may be initiated or increased after each cardioversion or defibrillation signal or may be delivered before and/or during a cardioversion or defibrillation signal to help prevent EMD, which can occur after the delivery of a cardioversion or defibrillation shock or otherwise be associated with such therapy. In some examples, INS 26 may sense the delivery of a cardioversion or defibrillation therapy. For example, INS 26 may anticipate the delivery of a cardioversion or defibrillation therapy based on a sensed EGM signal that indicates that such therapy is needed. As another example, electrodes of leads 28, 29 may detect defibrillation energy in body of patient 12 or an accelerometer sensor or acoustic/microphone sensor may detect severe mechanical jolt that may accompany the delivery of cardioversion or defibrillation therapy to patient 12. In such a situation, an accelerometer or acoustic/microphone sensor may be located within housing 122 of INS 26 as it may not be required to be at or near heart 14 to detect such defibrillation or cardioversion therapy. In some examples, ICD 16 may be configured to communicate with INS 26 to indicate imminent, occurring, and/or previously delivered defibrillation or cardioversion therapy. In some examples, for communication regarding stimulation therapy, ICD 16 and INS 26 may utilize one or more example techniques described in U.S. patent application Ser. No. 12/362,768, entitled "IMPLANTABLE MEDICAL DEVICE CROSSTALK EVALUATION AND MITIGATION," and filed Jan. 30, 2009, the entire content of which is incorporated herein by reference. Other example techniques are contemplated.

Figure 10:
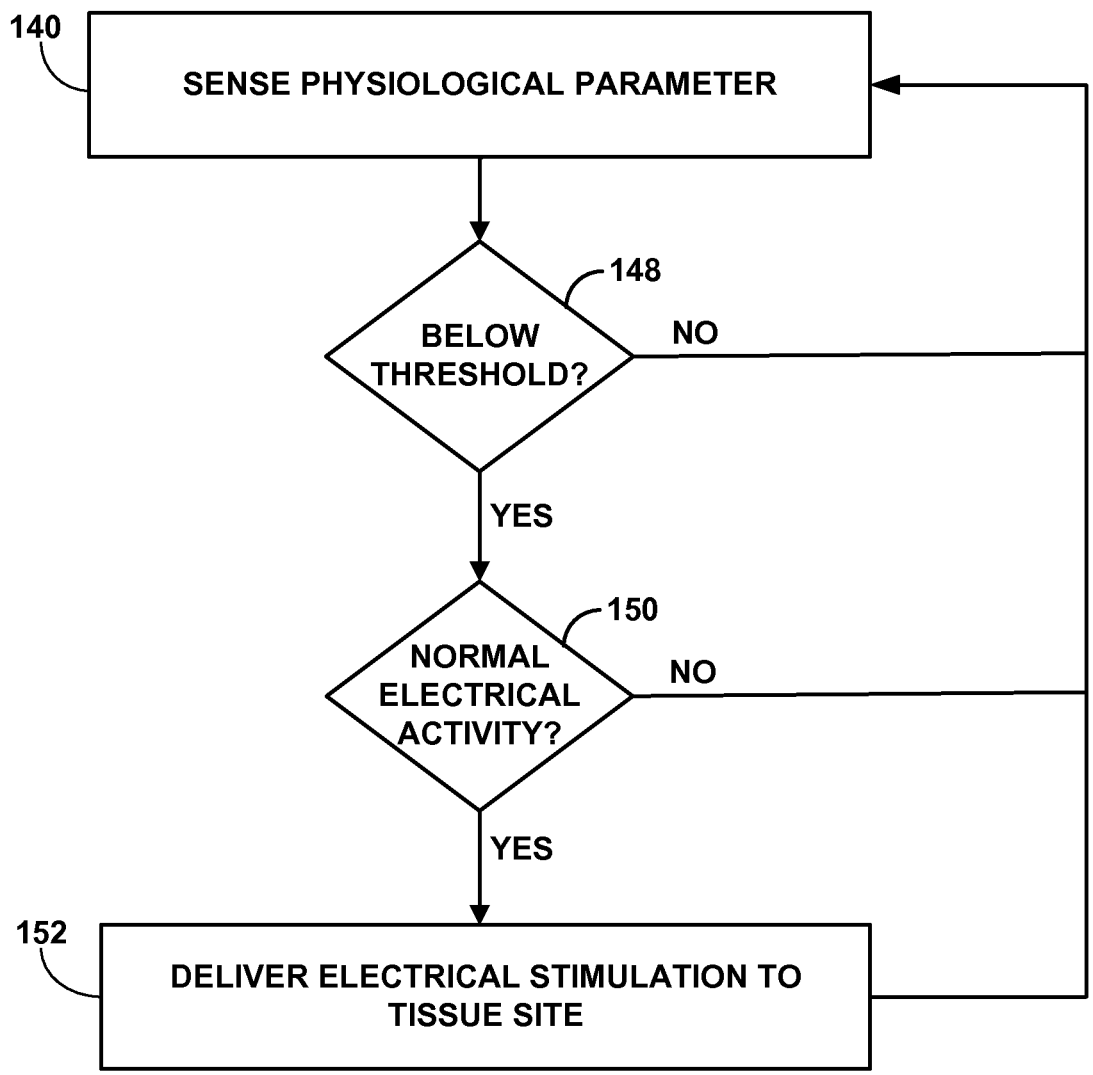
FIG. 10 is a flow diagram illustrating an example technique for determining when a heart is in an EMD state.

FIG. 10 is a flow diagram illustrating an example technique for detecting when heart 14 is in an EMD state. As indicated by FIG. 9, INS 26 may sense at least one physiological parameter of patient 12 via sensor 121 (FIG. 7) of lead 31 (140), as previously described, to determine a value of the parameter. In accordance with the technique shown in FIG. 10, INS 26 compares the sensed parameter value to a threshold value stored in memory 112 (148). In some examples, the threshold value may define a minimum parameter value observed in patient 12 when physiologically significant mechanical contraction of heart 14 is properly occurring. As previously indicated, a physiologically significant mechanical contraction may be, e.g., contractions necessary to supply the cardiac output (e.g., sufficient blood flow) to meet the needs of the patient's body. For example, in the case of blood pressure, the threshold value may define a minimum blood pressure value that is exhibited at the location monitored by sensor when physiologically significant mechanical contractions of heart 14 are present.

If the sensed parameter value is greater than or equal to that of the threshold value, INS 26 determines that mechanical contractions are likely occurring and INS 26 may continue monitoring the physiological parameter (140). Alternatively, if the sensed parameter value is less than the threshold value defined for the respective physiological parameter, INS 26 may determine that physiologically significant mechanical contractions of heart 14 are not occurring.

When INS 26 determines that mechanical contractions of heart 14 are not occurring based on the comparison of the physiological parameter to the threshold value, INS 26 subsequently determines whether the electrical activity of heart 14 is normal (150). For the purposed of this example, normal electrical activity of heart 14 may refer to electrical cardiac activity, e.g., an electrical cardiac signal indicative of a sinus rhythm, which may persist when heart 14 is in an EMD state.

If the electrical activity of heart 14 is normal electrical cardiac activity and INS 26 determined that heart 14 is not mechanically contracting in a physiologically significant manner, INS 26 may determine that heart 14 is in an EMD state. In such cases, processor 110 (FIG. 7) of INS 26 may control stimulation generator 114 to deliver electrical stimulation to patient 12, as described above, to treat the EMD state of heart 14 (152), e.g., by causing mechanical contraction of heart 14. Alternatively, if the electrical activity of heart 14 is abnormal rather than normal, then INS 26 may determine that heart 14 is not in an EMD state but rather in a state in which mechanical contraction and normal electrical activity of heart 14 is not present. In this case, INS 26 may notify ICD 16 that cardiac rhythm therapy is desirable.

In other examples of the technique shown in FIG. 10, processor 110 of INS 26 determines that heart 14 is not mechanically contracting in a physiologically significant manner, e.g., heart 14 is not providing sufficient output, by determining whether the sensed value of the physiological parameter is greater than or equal to a threshold value.

In addition, in other examples of the technique shown in FIG. 10, processor 110 of INS 26 determines that heart 14 is not mechanically contracting in a physiologically significant manner by determining whether the sensed value of the physiological parameter falls within a predetermined range of values. In some examples, the predetermined range of values indicates a range of physiological parameter values that are observed when physiological significant mechanical contraction of heart 14 is not present.

If the sensed value is within the range of the threshold value, INS 26 determines that sufficient mechanical contraction of heart 14 is not occurring in patient 12. In other examples, the predetermined range of values indicates a range of physiological parameter values that are observed when physiological significant mechanical contraction of heart 14 is present. If the sensed value is within the range of threshold value, INS 26 determines that sufficient mechanical contractions of heart 14 are occurring.

In some examples, the threshold parameter value is a mean or median value of the physiological parameter over a range of time, e.g., when heart 14 is known to not be in an EMD state, or a value at a discrete point in time. Alternatively or additionally, the threshold parameter value may define one or more trends of a sensed physiological parameter value over time, where the trend indicates a decrease in mechanical activity of heart 14. The trend may be stored as a value (e.g., a slope that indicate the change in the physiological parameter value over time) or a template signal that indicates the values for the change in the physiological parameter value over time.

For example, the threshold value may a define a specific behavior of the parameter value during a period of blood pressure change, e.g., an increase or decrease in value, over a period of time. The threshold parameter value may indicate whether the blood pressure change was approximately constant over the period of time or whether the blood pressure change included alternating periods of rapid change and leveling off. Furthermore, the threshold values may remain substantially the same throughout the life of the implanted device, or may be updated periodically. For example, the one or more sensed parameters may be continually or periodically monitored by INS 26 to dynamically define an average parameter value for patient 12, which may be used to determine whether heart 14 is in an EMD state.

Processor 110 may compare a trend in the sensed physiological parameter over time to the threshold value in order to determine whether heart 14 is in an EMD state. In the case of a trend template, if the trend in the sensed physiological parameter over time substantially correlates (e.g., correlates about 75% or greater, although other percentages of correlation may be used) to a stored template, processor 110 may determine that heart 14 is in an EMD state.

Figure 11:
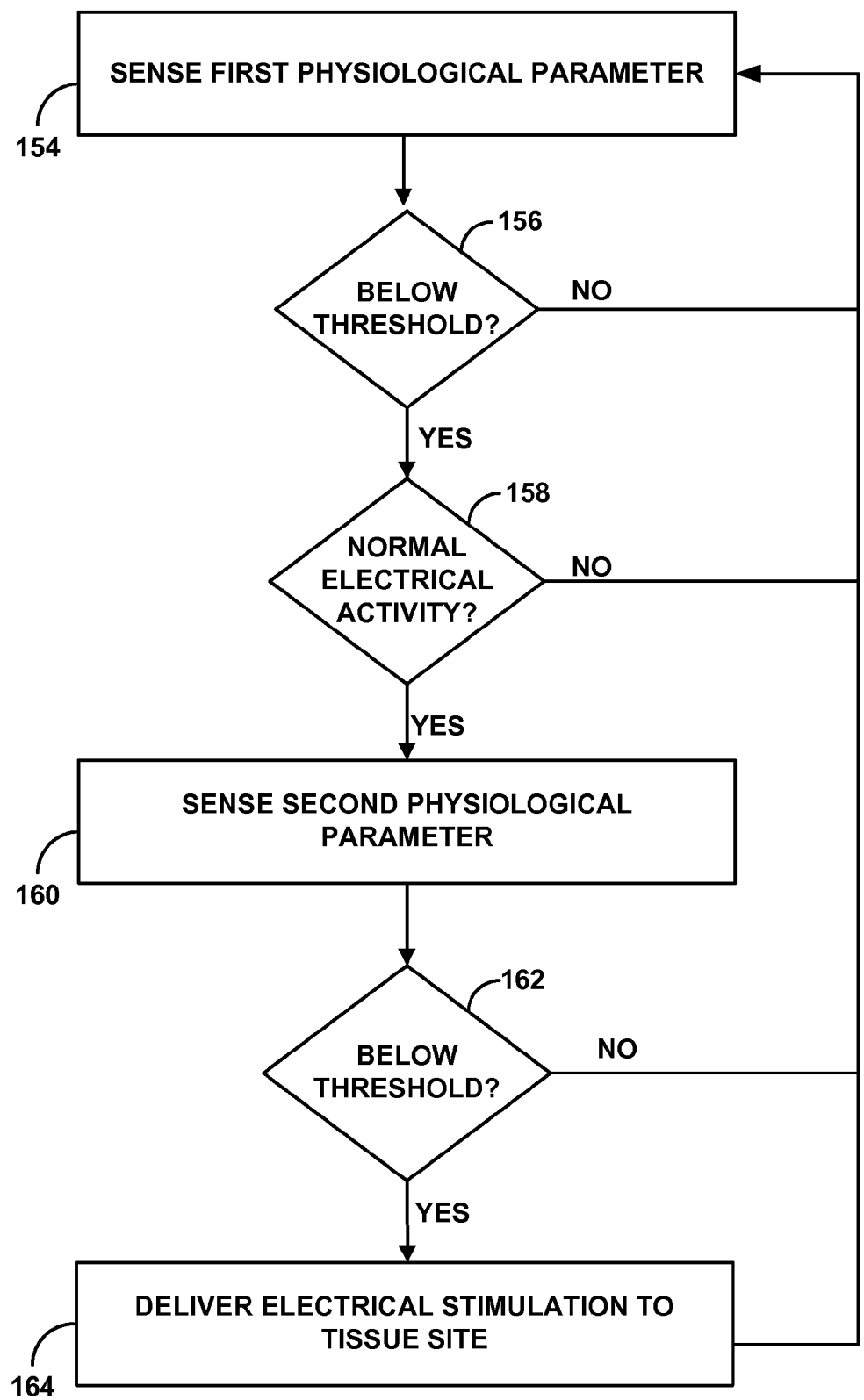
FIG. 11 is a flow diagram illustrating another example technique for determining when a heart is in an EMD state.

FIG. 11 is a flow diagram illustrating another example technique for determining when heart 14 is in an EMD state. The example technique is similar to that of the example technique illustrated in FIG. 10. However, in the example of FIG. 11, INS 26 may make a consistency determination based on a second sensed physiological parameter after at first sensed physiological parameter indicates an absence of mechanical contraction of heart 14. The first and second physiological parameters are different.

As indicated by FIG. 11, INS 26 senses a first physiological parameter, which may include one of the physiological parameters previously described, e.g., patient blood pressure, to determine a value of the respective parameter (154). Processor 110 of INS 26 compares the value of the first physiological parameter to a threshold value stored in memory 112 (156). The threshold value may be a first threshold value that is associated with the first physiological parameter. If the sensed value of the first physiological parameter is greater than or equal to the threshold value, then INS 26 may determine that physiologically significant mechanical contractions of heart 14 are present, and continue to monitor the first physiological parameter (154).

Alternatively, if the sensed value of the first physiological parameter is less than the first threshold value, processor 110 of determines that mechanical contractions of heart 14 are not occurring. In such a situation, processor 110 determines whether the electrical activity of heart 14 is normal, as described above with respect to FIG. 10 (156). If processor 110 determines that the electrical activity of heart 14 is not normal, processor 110 may determine that heart 14 is not is an EMD state, but rather in state in which both mechanical contractions and normal electrical activity are absent. However, if the electrical activity of heart 26 is normal electrical activity, then INS 26 may determination that heart 14 is in an EMD state.

In the example technique shown in FIG. 11, when INS 26 determines that heart 14 is in an EMD state based on the first sensed parameter, INS 26 does not directly proceed to deliver electrical stimulation to patient 12 to treat the EMD state. Instead, INS 26 determines whether a second physiological parameter indicative of contraction of heart 14 also indicates heart 14 is not contracting in a physiologically significant manner. In this way, processor 110 of INS 26 may make a consistency determination to determine whether a heart 14 is in an EMD state. Thus, after determining heart 14 is in an EMD state based on the first sensed parameter, INS 26 senses a second physiological parameter that is different than the first physiological parameter and determines a value of the respective parameter (160). Processor 110 compares the sensed value of the second physiological parameter to a second threshold value stored in memory 112 that corresponds to the second sensed parameter (162). The first and second threshold values may be different and can vary depending on the type of physiological parameter.

If the sensed value of the second physiological parameter is greater than or equal to the second threshold value, processor 110 determines that the second physiological parameter value does not indicate heart 14 is in an EMD state. Accordingly, processor 110 determines that the first EMD state determination based on the first sensed physiological parameter is inconsistent with the second EMD state determination based on the second physiological parameter. In such a case, INS 26 withholds delivery of electrical stimulation to patient 12, and may repeat the process.

On the other hand, if the value of the second physiological parameter is less than the threshold value, processor 110 of INS 26 determines that heart 14 is in an EMD state. Accordingly, processor 110 may determine that the first EMD state determination based on the first sensed physiological parameter is consistent with the second EMD state determination based on the second sensed physiological parameter. Upon determining that heart 14 is in an EMD state based on both the first and second physiological parameters, processor 110 controls stimulation generator 114 to deliver electrical stimulation to a tissue site of patient 12 to modulate afferent nerve activity and/or inhibit efferent nerve activity, as described above, and treat the EMD state of heart 14 (164).

The technique shown in FIG. 11 may be a more robust technique for determining that heart 14 is in an EMD state correctly reflects the actual state of heart 14, and may be useful for increasing the likelihood that the determination that heart 14 is in an EMD state is correct. Although FIG. 11 is described with respect to making two EMD state determinations based on two separate physiological parameters of patient 12, in other examples, processor 110 of INS 26 may make any suitable number of EMD state determinations based on any suitable number of sensed physiological parameters of patient 12. For example, INS 26 may monitor more than two types of physiological parameters of patient 12.

Figure 12:
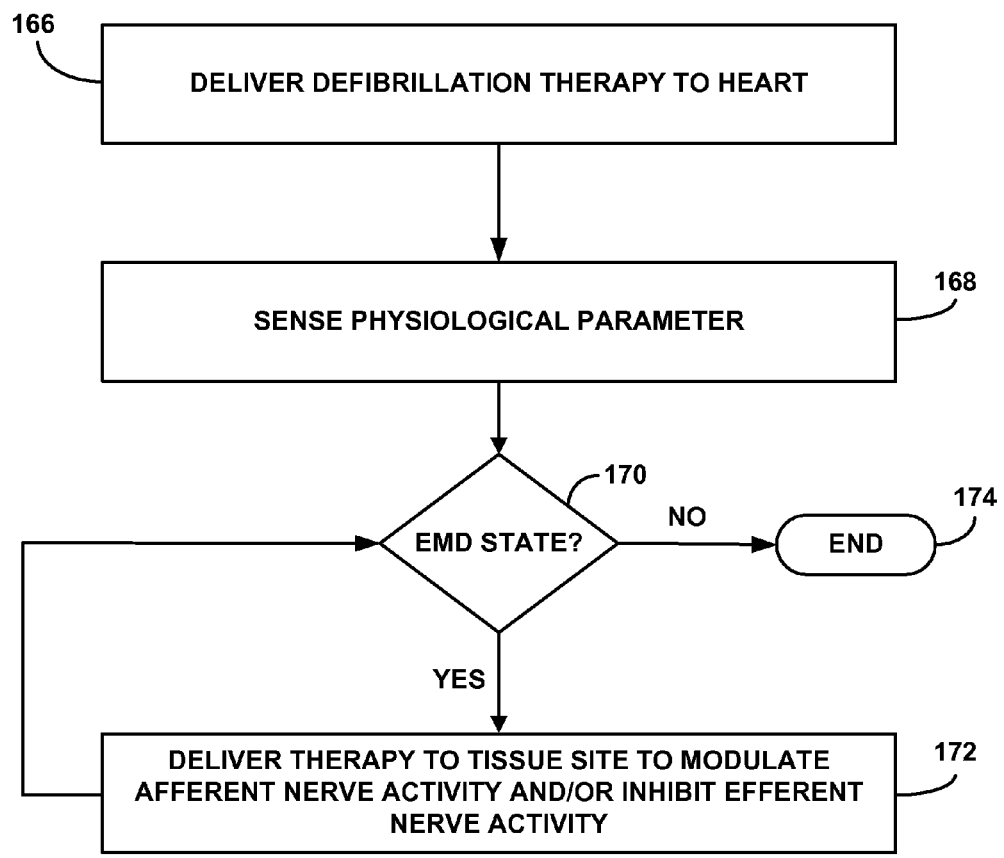
FIG. 12 is a flow diagram illustrating an example technique for monitoring a heart of a patient for an EMD state following delivery of defibrillation therapy to the heart.

FIG. 12 is a flow diagram illustrating an example technique for monitoring heart 14 for an EMD state relative to delivery of defibrillation therapy to heart 14 by ICD 16. While the example of FIG. 12 is described with respect to delivery of defibrillation therapy to heart 14, other examples of the technique may include delivery of a cardioversion therapy to heart 14. Although not limited to such situations, heart 14 may be susceptible to EMD following the delivery of defibrillation and/or cardioversion therapy to heart 14 by ICD 16. Accordingly, in some examples, INS 26 may be configured to monitor for an EMD state of heart 14 in conjunction with the delivery of such therapy to heart 14 of patient 12 via ICD 16.

As indicated by FIG. 12, ICD 16 delivers defibrillation therapy to patient 12 in the form of electrical stimulation (e.g., a shock) delivered via one or more electrodes on leads 18, 20, 22 (166). For example, ICD 16 may deliver the therapy based on the determination that heart 14 is in a fibrillation state. While the therapy delivered by ICD 16 may successfully terminate the fibrillation of heart 14, heart 14 may be susceptible EMD immediately after the delivery of the defibrillation therapy.

INS 26 may detect the delivery of the defibrillation therapy to heart 14 using any suitable technique. In some examples, INS 26 senses the electrical signals associated with the delivery of the defibrillation therapy via one or more electrodes of lead 28 and/or sensor 121 of lead 31. In other examples, before, during, or after the delivery of a the defibrillation therapy to heart 14, ICD 16 communicates information indicative of the delivery of the defibrillation therapy to INS 26 via the respective telemetry modules 98, 118. In response to detecting the delivery of the defibrillation therapy to heart 14, processor 110 of INS 26 may determine whether heart 14 is in an EMD state.

In one example, as shown in FIG. 12, before, during or after delivery of the defibrillation therapy by ICD 16, INS 26 senses a physiological parameter indicative of the contraction of heart 14. As previously described, physiological parameters indicative of the contraction of heart 14 include blood pressure, blood flow, blood oxygen saturation level, movement of cardiac muscles, heart sounds, heart images, and tissue perfusion.

In some examples, INS 26 immediately begins sensing the physiological parameters after receiving the indication that ICD 16 delivered the defibrillation therapy or after sensing the delivery of the defibrillation therapy. In other examples, INS 26 may begin sensing the physiological parameters after the passage of an appropriate delay period after the delivery of the defibrillation therapy. For example, such a delay period may correspond to the time generally required for one of more of the physiological parameter sensed by INS 26 to reach a level indicative of the absence of mechanical contraction of heart 14.

Similar to that described above, if INS 26 determines that heart 14 is in an EMD state (170), INS 26 delivers appropriate electrical stimulation to patient 12 to cause the desired mechanical contractions of heart 14 and terminate the EMD state of heart 14 (172). On the other hand, if INS 26 does not determine that heart 14 is in an EMD state based on the physiological parameters sensed after the delivery of the defibrillation pulse, INS 26 may stop sensing the physiological parameters (174). In some cases, INS 26 may continue to monitor for an EMD state of heart 14 for time period corresponding the period in which heart 14 is likely to enter an EMD state after defibrillation therapy is delivered to heart 14. In this manner, INS 26 may be configured to monitor the one or more appropriate physiological parameters at times that heart 14 may be most susceptible to being in an EMD state, rather than continuously monitoring patient 12 for an EMD state.

As indicated in FIG. 12, INS 26 may continue delivering the first stimulation therapy until processor 110 determines heart 14 is no longer in an EMD state. This determination may be made according to the same sensed physiological parameters used to initially determine that heart 14 was in an EMD state. For example, after or during the delivery of the first neurostimulation therapy, processor 110 may determine whether heart 14 of patient 12 is mechanically contracting and whether a relatively normal sinus rhythm is detected. In some examples, INS 26 may deliver the first stimulation therapy to patient 12 substantially continuously. Such an example may correspond to configurations in which an accurate EMD state determination is not prevented by the delivery of the first stimulation therapy to patient 12, e.g., sensing module 119 may accurately sense the one or more physiological parameters regardless of whether the electrical stimulation is being delivered to the tissue site. In other examples, INS 26 may deliver the first stimulation therapy on a periodic basis rather than substantially continuously, e.g., in configurations in which an accurate EMD state determination is prevented during the delivery of the stimulation therapy by INS 26. For example, in such cases, INS 26 may deliver the first stimulation therapy to the tissue site for set periods of time with periodic pauses that to allow for an accurate determination as to whether heart 14 is still in an EMD state, or if the EMD state of heart 14 has been successfully treated by the stimulation therapy.

In any case, INS 26 continues to deliver first stimulation therapy to patient 12 until processor 110 determines that heart 14 is no longer in an EMD state based on the one or more sensed physiological parameters (174). In this manner, INS 26 may continue to deliver the first stimulation therapy to the tissue site until the sensed physiological parameters indicate that heart 14 is no longer in an EMD state.

Alternatively or additionally, INS 26 may deliver the first stimulation therapy for only a predetermined amount of time. For example, INS 26 may be configured to deliver the first stimulation therapy until a predetermined first time period, which may be defined according to the typical amount of time required to treat heart 14 in an EMD state via the first therapy, has expired or processor 110 determines that heart 14 is no longer in an EMD state. In this manner, INS 26 may be prevented from continuously delivering the first stimulation therapy to the tissue site for an unnecessary length of time in the event of an inaccurate EMD state determination by processor 110 of INS 26. In examples, electrical stimulation therapy may be delivered to the tissue site of patient 12 to treat EMD for approximately 1 second to approximately 10 minutes. In some examples, INS 26 may continue to deliver stimulation to patient 12 for a predetermined amount of time subsequent to the termination of the EMD state. The predetermined amount of time may be a constant amount of time or may be a function of the amount of time needed to treat the EMD state, e.g., the longer the amount of time need to terminate the EMD state, the longer the amount of time the therapy will be delivered after the EMD state is terminated.

Figure 13:
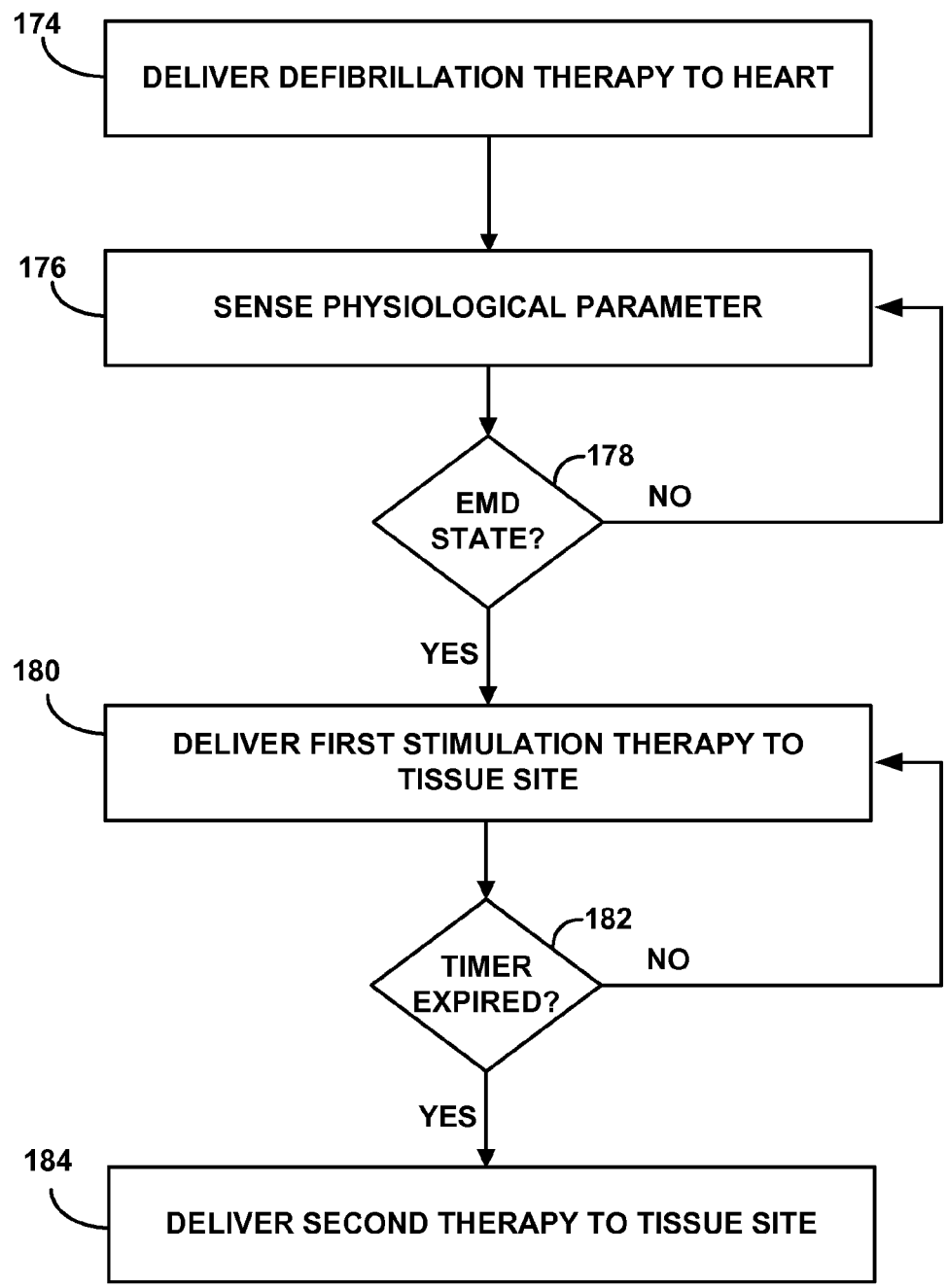
FIG. 13 is a flow diagram illustrating another example technique for monitoring a heart of a patient for an EMD state following the delivery of defibrillation therapy to the heart.

FIG. 13 is a flow diagram illustrating an example technique for monitoring heart 14 for an EMD state relative to delivery of a defibrillation therapy to heart 14 by ICD 16. The example technique is similar to that previously described with respect to FIG. 12. For example, ICD 16 may deliver defibrillation therapy to patient 12 in the form of electrical stimulation delivered via one or more electrodes on leads 18, 20, 22 (174). INS 26 may sense at least one physiological parameter of patient 12 after delivery of the defibrillation therapy (176), which may then be used to determine an EMD state of heart 14 (178), e.g., as described above with respect to FIG. 10. In the example shown in FIG. 13, if the EMD state is detected, processor 110 of INS 26 controls stimulation generator 114 to deliver a first stimulation therapy during a first time period, and then delivering a second stimulation therapy during a second time period, e.g., upon expiration of the first time period.

In particular, when processor 110 of INS 26 determines that heart 14 is in an EMD state (178), processor 110 may control stimulation generator 114 to deliver a first stimulation therapy to a tissue site to modulate afferent nerve activity and/or inhibit efferent nerve activity (180). In some examples, the first therapy delivered by INS 26 may include relatively high intensity stimulation. Delivery of the high intensity stimulation may be particularly effective in treating the EMD state of heart 14, e.g., by "waking-up" the brain of patient 12 to the EMD state of heart 14. In some examples, the first stimulation therapy having a relatively high intensity may be achieved by delivering a stimulation signal comprising a relatively high pulse rate and/or relatively high pulse amplitude. In some examples, the first therapy may have a frequency (e.g., a pulse rate) between approximately 10 to 200 Hz, such as, e.g., 50-100 Hz, although other pulse rates are contemplated. In general, the pulse rate may be set at as high of frequency possible, with consideration to the stimulation limitations of INS 26 and patient 12. Stimulation amplitude of the first therapy may range from approximately 0.5 volts to approximately 12 volts, such as, e.g., approximately 5 volts to approximately 10 volts or approximately 1 volt to approximately 10 volts, although other stimulation amplitudes are contemplated. In some examples, the amplitude may be approximately equal to the maximum stimulation amplitude tolerable by patient 12.

While the relatively aggressive first stimulation therapy may be effective in terminating the EMD state of heart 14, depending on the exact parameters of the first therapy delivered, it may be safe to only deliver the first therapy to the tissue site for a short period of time to avoid one or more undesirable side-effects. For example, in some cases, the first stimulation therapy having a relatively high intensity may stress tissue if the stimulation is delivered for too long. Accordingly, INS 26 may be configured to deliver the first stimulation for only a first period of time that is selected to minimize stress to tissue. As indicated in FIG. 13, processor 110 of INS 26 may control stimulation generator 114 to deliver the first stimulation therapy to patient until a timer, which defines the first time period, expires (182).

The first time period during which the first stimulation therapy is delivered may generally be any amount of time approximately less than or equal to that of the maximum period that INS may deliver neurostimulation according to the first therapy program without stressing tissue. In some example, INS 26 may be pre-programmed with a "safe" time period for a given stimulation parameter value or set of stimulation parameter values based on which the first time period is defined. Additionally or alternatively, INS 26 may be configured such that a physician may define the first time period, e.g., via programmer 24, to allow for first time period that is tailored to a particular patient. In examples in which the first stimulation therapy includes relatively high intensity stimulation, the first time period may be less than or approximately equal to 1 minute, e.g., less than or approximately equal to 30 seconds.

In any case, once the first time period timer (182) has expired, INS 26 may terminate delivery of the first stimulation therapy and initiate delivery of a second stimulation therapy (184). The first and second stimulation therapies may be defined by therapy programs stored in memory 112 of INS 26 (FIG. 7) or a memory of another device. The first and second therapy programs may have at least one different stimulation parameter. In some examples, the second stimulation therapy has a lower intensity than the first stimulation therapy. The stimulation intensity may be a function of the stimulation parameter values, such as the pulse rate, pulse width, duty cycle, amplitude, and the like. In some examples, the second therapy program may have a lower frequency and/or lower stimulation amplitude (e.g., current or voltage amplitude) than the first therapy program. The lower stimulation intensity of the second stimulation therapy may allow for continued delivery of electrical stimulation for a longer period of time compared to the first stimulation therapy without a significant likelihood of causing one or more undesirable side effects. In other cases, the second stimulation therapy may define a period during which INS 26 does not deliver electrical stimulation to the tissue site of patient 12, effectively ending delivery of electrical stimulation to patient 12 after the expiration of the first time period. In some examples, the intensity of the first and/or second stimulation therapies may be ramped up (e.g., by increasing amplitude or duration of duty cycle) to reduce muscle twitch or pain experienced by patient due to the stimulation.

Similar to that of the first stimulation, the second stimulation therapy may be delivered for a second time period following the first time period. The second time period may be defined by a timer, e.g., similar to that shown in FIG. 13 for defining the first time period for delivery of the first stimulation therapy. In some examples, the second time period may be longer than that of the first time period for the first stimulation therapy, e.g., in cases in which the second stimulation therapy is of a lower intensity than the first therapy thus allowing the second stimulation therapy to be delivered for a longer period of time without a significant likelihood of causing one or more undesirable side effects. Once the second time period has expired, the delivery of the second stimulation therapy from INS 26 to patient 12 may be terminated.

In some examples, upon expiration of the second time period for delivery of second stimulation therapy, INS 26 or other device may determine whether heart 12 is in an EMD state, which can be the same EMD state occurrence as the previously detected EMD state (178) or may be a separate occurrence that is, e.g., separated in time from the previous EMD state detection. INS 26 or other device may determine that heart 12 is in the EMD state using one or more the techniques described herein. For examples, INS 26 may sense at least one physiological parameter of patient 12 after delivery of the defibrillation therapy, which may then be used to determine an EMD state of heart 14, e.g., as described above with respect to FIG. 10.

If the EMD state of heart 14 is detected after the delivery of the second therapy (184), INS 26 may initiate delivery of stimulation therapy to treat the EMD state. In some examples, the stimulation therapy may have the same or similar stimulation parameters as that of the first and/or second stimulation therapies described above with regard to FIG. 13, while in other examples one or more of the stimulation therapy parameters values may be adjusted from that of the first and/or second stimulation therapies to treat the new EMD state. If INS 26 does not detect an EMD state after the second therapy is terminated, INS 26 may continue to monitor patient 12 to detect if and when heart 14 enters an EMD state so that stimulation may be delivered to treat the EMD state at that time. In such an example, system 10 may monitor and treat patient 12 for occurrences of EMD in a closed-loop manner.

Figure 14:
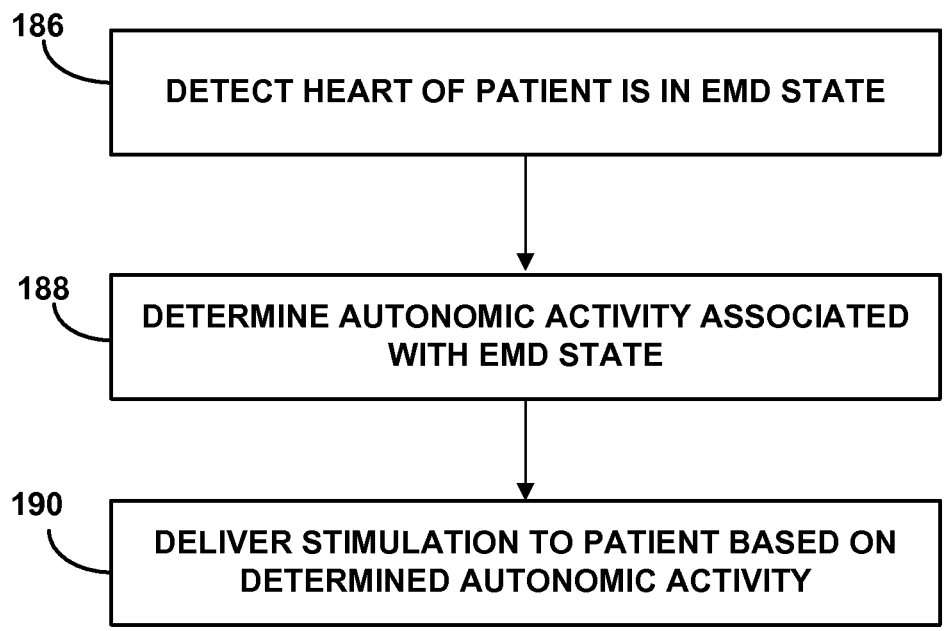
FIG. 14 is a flow diagram illustrating an example technique for delivering stimulation to a patient when the heart of the patient is in an EMD state.

FIG. 14 is a flow diagram illustrating an example technique for delivering electrical stimulation to a patient when a heart of the patient is in an EMD state. As described above, in some examples, a therapy system, such as therapy system 10 or therapy system 80 may be configured to monitor autonomic nervous system activity of patient 12 to determine autonomic nervous system activity associated with an EMD state. For ease of illustration, the example technique of FIG. 14 is described with regard to therapy system 10 but is not limited in implementation to such therapy system configurations. Moreover, although the example technique of FIG. 14 is primarily described with regard to INS 26, one or more aspects of the technique may be performed by another device, such as ICD 16, programmer 24 or ICD 80 either in combination with INS 26 or exclusive from that of INS 26.

As illustrated in FIG. 14, processor 110 (FIG. 7) of INS 26 detects that heart 14 is in an EMD state (186), e.g., using one or more of the techniques described herein for detecting that heart 14 is in EMD state. Upon detecting that heart 14 is in an EMD state, processor 110 (FIG. 7) determines autonomic activity associated with the EMD state of heart 14 (188). As discussed above, the autonomic nervous system activity associated with the EMD state of heart 14 can be indicated by the activity level of sympathetic and parasympathetic nervous system activity relative to each other, or just one of the sympathetic or parasympathetic nervous system activities. In addition, the autonomic nervous system activity associated with the EMD state of heart 14 can be the autonomic nervous system activity temporally correlating to the detection of the EMD state by processor 110, and, in some examples, includes the time period before and/or after detection of the EMD state by processor 110. A loop recorder or the like can be used to store sensed signals indicative of autonomic nervous system activity (e.g., sensed sympathetic nervous system activity) for the time period before the detection of the EMD state. Processor 110 (FIG. 7) of INS 26 then controls the delivery of therapy to patient 12 based on the autonomic nervous system activity determined to be associated with the EMD state of heart 14 (190).

The monitored autonomic activity of patient 12 analyzed by INS 26 may include sympathetic nervous system activity and/or parasympathetic nervous system activity of patient 12. For ease of illustration, examples of the disclosure may primarily be described with regard to sympathetic activity. Processor 110 can determine the nerve activity of a sympathetic or parasympathetic nerve using any suitable technique. In some examples, sensing module 119 (FIG. 7) generates an electrical signal that is indicative of an electrical nerve signal generated by a nerve, such as the target sympathetic or parasympathetic nerve used to determine autonomic nervous system activity or a branch thereof, in response to an electrical stimulation signal delivered by the electrodes of lead 28 or lead 31. The electrical nerve signal may be sensed between two or more electrodes of lead 28 or lead 31 (FIG. 7). Processor 110 may analyze the electrical nerve signal for an indication of autonomic nervous system activity, for example, by measuring an amplitude of the electrical nerve signal and comparing the measured value to a threshold value. The threshold value may be, for example, an amplitude or other characteristics of a sensed electrical signal.

Autonomic activity associated with the EMD state of heart 14 may be autonomic activity sensed just prior to or during the occurrence of an EMD state of heart 14. In some examples, the autonomic activity associated with the EMD state may be an underlying cause of the EMD state of heart 26. For example, in some cases, heart 14 may be in an EMD state due in part to elevated sympathetic nervous system activity. In other examples, heart 14 may be in an EMD state due in part to decreased sympathetic nervous system activity. By determining the autonomic nervous system activity associated with heart 14 when in an EMD state, processor 110 of INS 26 may control delivery of therapy to address the autonomic activity associated with the EMD state of heart 14 in a manner that effectively treats the EMD state of heart 14. In particular, processor 110 controls stimulation generator 114 to generate and deliver stimulation therapy to patient 14 that addresses at least one contributing factor to the EMD state. In this way, the therapy delivered by INS 26 is relevant to the particular EMD state of patient 12.

As an illustration, processor 110 of INS 26 may determine that the autonomic nervous system activity associated with the detected EMD state of heart 26 includes a depressed level of sympathetic activity. Based on the depressed level of sympathetic nervous system activity determined to be associated with the EMD state of heart 14, processor 110 of INS 26 may control delivery of therapy to patient 12 to increase the level of sympathetic nervous system activity in patient 12. Such stimulation may effectively treat the detected EMD state of heart 12, e.g., by promoting mechanical contraction of heart 12.

In some examples, after delivering stimulation therapy to patient 12 that is configured to increase sympathetic nervous system activity, e.g., when a depressed level of sympathetic nervous system activity is associated with a detected EMD state of heart 14, INS 26 may subsequently adjust the stimulation therapy to then reduce sympathetic nervous system activity for patient 12. For example, INS 26 may deliver a first stimulation therapy generated according to a first therapy program that is configured to increase sympathetic activity may be delivered to patient for a first time period. The first time period may be selected to effectively bring heart 14 out of the EMD state with the first stimulation therapy configured to increase sympathetic nervous system activity. Following the expiration of the first time period and the corresponding increase in sympathetic activity of patient 12, processor 110 of INS 26 may modify the stimulation being delivered to patient 12 to deliver a second stimulation therapy to patient 12 that is configured to decrease sympathetic activity in patient 12.

In such an example, while the first stimulation therapy may increase the sympathetic activity to a level that effectively brings heart 14 out of the detected EMD state, such a level of sympathetic activity may not be sustainable and/or may lead to undesired side effects. As such, once INS 26 delivers the first therapy to, in essence, increase the contractility of heart 14 and bring heart 14 out of an EMD state by increasing the sympathetic nervous system activity, INS 26 may deliver a second therapy generated according to a second therapy program that reduces sympathetic activity of patient 12, e.g., to a baseline level or some other level of sympathetic activity to avoid undesired side effects. In some examples, the second stimulation therapy may be delivered to reduce sympathetic activity to be less than that experience by patient due to the first stimulation therapy but greater than the sympathetic activity associated with the EMD state. The first and second therapy programs have at least one different stimulation parameter value.

As another example, in other cases, processor 110 of INS 26 may determine that autonomic activity associated with the detected EMD state of heart 14 includes a relatively high level of sympathetic activity. Upon determining heart 14 is in an EMD state and the EMD state is associated with a relatively high level of sympathetic activity, processor 110 can control stimulation generator 114 to generate and deliver stimulation therapy to patient 12 in a manner that decreases sympathetic activity of patient 12. Again, such stimulation may effectively treat the detected EMD state of heart 12, e.g., by promoting mechanical contraction of heart 12, by decreasing sympathetic nervous system activity from that associated with the EMD state of heart 12.

As described above, system 10 may monitor autonomic activity of patient 12 using any suitable methodology. In some examples, processor 110 of INS 26 (or a processor of another device such as ICD 16) may determine autonomic activity of patient 12 by monitoring the electrical activity of heart 14. As described above, sensing module 96 of ICD 16 may monitor signals from at least one of electrodes 50, 52, 54, 56, 58, 60, 68, 72, 74, and 76 in order to monitor electrical activity of heart 14, e.g., via an EGM signal. In such an example, processor 110 may receive the sensed electrical activity of heart 14 from ICD 16 and analyze the sensed electrical activity of heart 14 to determine the heart rate of heart 14 and/or heart rate variability (e.g., P-P interval variability and/or R-R interval variability) that may be indicative of autonomic nervous system activity. Alternatively, processor 90 of ICD 16 may make the determination and transmit an indication of the autonomic nervous system activity to processor 110.

As one example, sympathetic activity of a patient 12 may be monitored and determined by sensing the heart rate of heart 14. During an EMD state, the heart rate of heart 14 may be determined based on the sensed electrical signals of heart 14 (e.g., an ECG or EGM) despite that fact heart 26 is generally not mechanically contracting in a physiologically significant manner due to the EMD state. Processor 110 of INS 26 (or another processor) can compare the heart rate indicated by the sensed electrical activity of heart 14 during an EMD state or just prior to the occurrence of an EMD state to a threshold value to determine if the heart rate is relatively low, e.g., as compared to an average heart rate of patient 12. If processor 110 determines that the heart rate is relatively low, processor 110 may determine that the sympathetic activity of patient 12 is depressed. Sensed electrical activity of heart 14 that reflects a relatively low heart rate, such as, e.g., about 20 to 30 beats per minute (BPM) compared to a "normal" heart rate of about 60 to about 70 BPM, may be indicate depressed sympathetic activity. In response to the depressed sympathetic activity, INS 26 (or ICD 16) may deliver stimulation therapy to patient 12 in a manner that increases sympathetic activity to treat the EMD state of heart.

Conversely, if processor 110 determines that the heart rate indicated by the sensed electrical activity of heart 14 during an EMD state or just prior to the occurrence of an EMD state is relatively high, e.g., as compared to an average heart rate of patient 12 or one or more threshold heart rate values or ranges, processor 110 may determine that the sympathetic activity of patient 12 is overexcited. In some examples, sensed electrical activity of heart 14 that reflects a relatively high heart rate, such as, e.g., about 100 to 120 beats per minute (BPM), may be indicate overexcited sympathetic activity. As described above, in response, INS 26 (or ICD 16) may deliver stimulation therapy to patient 12 to decrease sympathetic activity to treat the EMD state of heart 14. The low heart rate, high heart rate, and/or normal heart rate may be predetermined and stored by ICD 16, INS 26 or another device. In other examples, the normal heart may be determined based on, for example, an average sensed heart rate for a predetermined period of time preceding the detection of the EMD state. In this way, the "normal" heart rate may be a dynamically changing value.

Additionally or alternatively, heart rate variability (e.g., P-P interval variability and/or R-R interval variability) may also be analyzed by processor 110 (or another processor) to monitor and determine autonomic activity to treat the detected EMD state of patient 14. In some examples, sensed electrical activity of heart 14 that reflects an increase in heart rate variability may indicate overexcited parasympathetic nervous system activity. In this way, heart rate variability may be used as an indicator for the nature of the autonomic nervous system activity associated with a detected EMD state.

As another example, processor 110 of INS 26 (or another device) may determine autonomic activity of patient 12 associated with an EMD state by monitoring electrical nerve activity of patient 12. For example, sensing module 119 may monitor electrical activity of a nerve (e.g., a vagal nerve) via sensor 121 (FIG. 7) and generate an electrical signal indicative of the electrical nerve activity. Processor 110 may receive the electrical signal and extract signal characteristic directly from the signal or from a parameterized signal or data generated based on the raw electrical nerve signal in order to determine whether the electrical nerve activity is indicative of an excited or depressed parasympathetic nervous system activity level and/or an excited or depressed sympathetic nervous system activity level.

In such an example, processor 110 (FIG. 7) may analyze the sensed electrical signal when heart 14 is determined to be in an EMD state. If nerve activity is for the vagus nerve or another parasympathetic nerve and the sensed vagal nerve electrical activity indicates a relatively high amount of vagal nerve activity, then INS 26 may determine that the parasympathetic activity of patient 12 is overexcited. In such a case, the detected EMD state may be caused by vagal nerve overexcitation. Processor 110 can compare a signal characteristic of the electrical nerve signal to a predetermined threshold value (e.g., stored in memory 112) to determine whether the sensed vagal nerve (or other parasympathetic nerve) electrical activity indicates a relatively high amount of vagal nerve activity. In some examples, processor 110 can supplement the determination by determining whether the heart rate of patient 12 is also relatively low. In response to the vagal overexcitation, processor 110 can controls stimulation generator 114 of INS 26 (or ICD 16) may deliver stimulation therapy to patient 12 to increase sympathetic activity to treat the EMD state of heart.

Processor 110 can also apply a similar technique to determine whether an electrical nerve signal generated by a sympathetic nerve indicates a relatively high amount of sympathetic activity. For example, processor 110 can compare a signal characteristic of the sensed electrical nerve signal of the sympathetic nerve to a predetermined threshold value (e.g., stored in memory 112) to determine whether the sensed nerve electrical activity indicates a relatively high amount of sympathetic nervous system activity. Processor 110 can then select the EMD stimulation therapy parameters based on the determination, e.g., by selecting a therapy program from memory 112 or adjusting one or more stimulation parameter values of a particular therapy program.

As another example, processor 110 (or another processor) may determine autonomic activity of patient 12 via intracardiac nerve recording. For example, INS 26 and/or ICD 16 may be configured to monitor electrical activity at the atrioventricular (AV) node. The AV node of patient 12 may include a large number of parasympathetic nerve fibers. As such, electrical activity monitored at the AV node may be used as an indicator of excited or depressed parasympathetic nervous system activity. If ICD 16 senses the electrical activity at the AV node, ICD 16 can transmit an indication of the electrical activity or the raw signal to INS 26 via the respective telemetry modules or another suitable communication technique. In some examples, the stimulation therapy delivered to patient 12 from INS 26 to treat heart 14 when in an EMD state may be based on the parasympathetic activity indicated by the sensed AV node electrical activity.

Similarly, processor 110 may determine autonomic activity of patient 12 via sympathetic ganglion recording. For example, INS 26 may be configured to monitor electrical activity at one or more sympathetic ganglia of patient 12. Sympathetic ganglia of patient 12 may include a high number of sympathetic nerve fibers. As such, electrical activity monitored at one or more sympathetic ganglia may be used as an indicator of excited or depressed sympathetic nervous system activity. In some examples, the stimulation therapy delivered to patient 12 from INS 26 to treat heart 14 when in an EMD state may be based on the sympathetic activity indicated by the sensed sympathetic ganglion electrical activity. Additionally or alternatively, in a similar fashion, processor 110 of INS 26 may monitor parasympathetic ganglion electrical activity, e.g., to identify depressed or overexcited parasympathetic activity.

Figure 15:
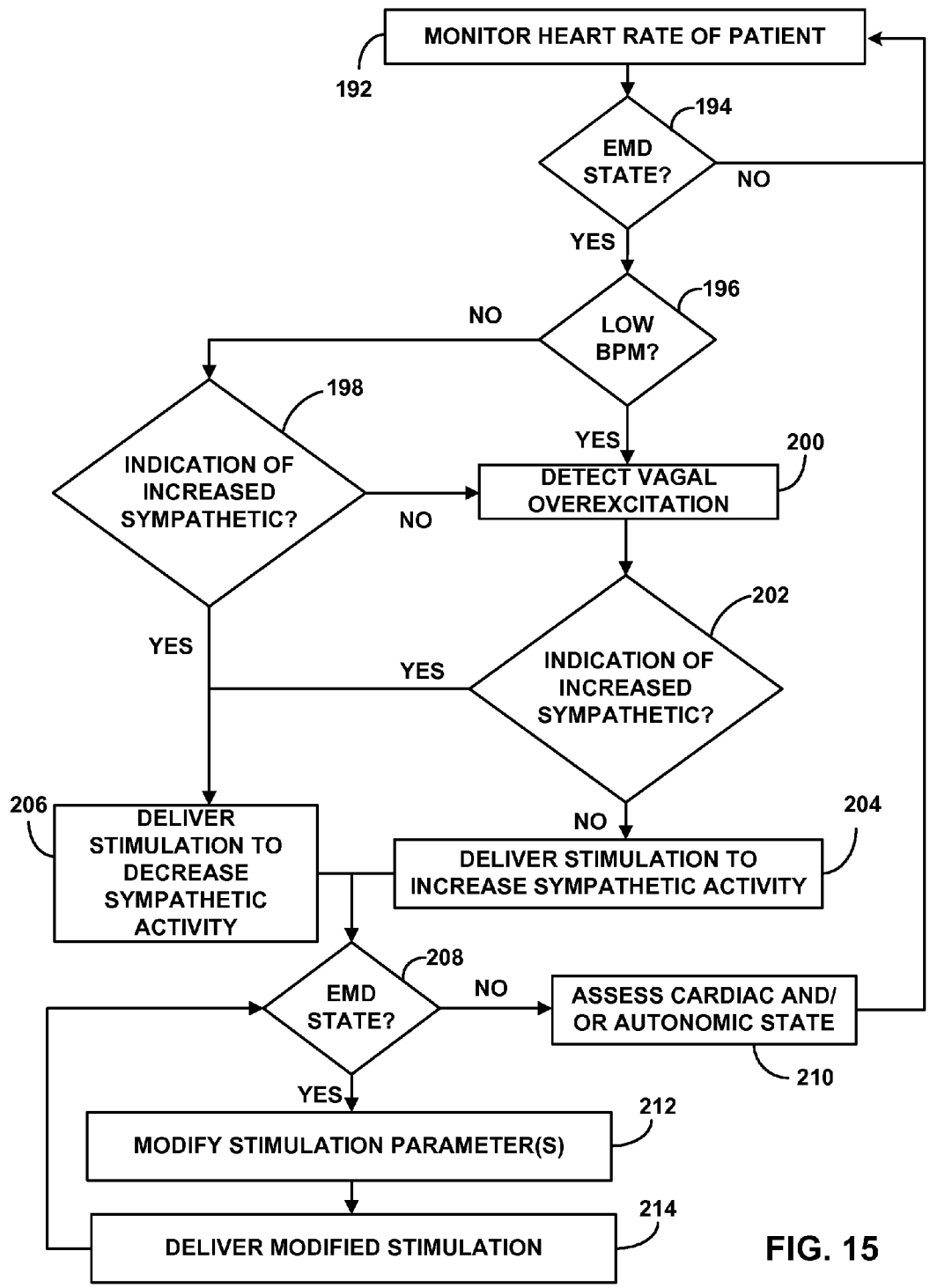
FIG. 15 is a flow diagram illustrating an example technique for delivering stimulation to a patient when the heart of the patient is in an EMD state.

FIG. 15 is a flow diagram illustrating an example technique for delivering stimulation to patient 12 when heart 14 of patient 12 is in an EMD state. Processor 110 of INS 26 or a processor of another device, or a combination of processors of one or more devices, can apply the technique shown in FIG. 15, such as by executing machine readable instructions that are stored in memory 112. Processor 110 can apply the technique shown in FIG. 15 to identify autonomic activity associated with a detected EMD state, and control stimulation therapy to treat the EMD state that is configured based on the autonomic nervous system activity associated with the EMD state. For ease of illustration, the example technique of FIG. 15 is described with regard to therapy system 10 but is not limited in implementation to such therapy system configurations. Moreover, although the example technique of FIG. 15 is primarily described with regard to INS 26, one or more aspects of the technique may be performed by ICD 16, programmer 24 or ICD 80 either in combination with INS 26 or exclusive from that of INS 26.

As illustrated in FIG. 15, INS 26 monitors by the heart rate of patient 12, which is determined based on electrical activity of heart 14 sensed via sensing module 119 and sensor 121 (192). Heart rate can be indicated by, for example, the heart beats per minute (BPM). In other examples, ICD 16 can transmit an indication of the heart rate, e.g., a heart rate value, the raw electrical cardiac signal or a parameterized indication of the electrical cardiac signal to INS 26 via the respective telemetry modules 98, 118, and processor 110 can determine the heart rate based on the information received from ICD 16. Processor 110 can periodically determine the heart rate of patient 12, e.g., at predetermined intervals of time, or processor 110 can continuously determine heart rate.

While monitoring the heart rate of patient 12, processor 110 (FIG. 7) of INS 26 may determine whether heart 14 is in an EMD state (194), e.g., using one or more of the techniques described herein for detecting that heart 14 is in EMD state. If processor 110 determines that heart 14 is in an EMD state, processor 110 analyzes a sensed electrical cardiac signal (e.g., EGM or ECG) of patient 12 to determine whether the electrical cardiac signal indicates a relatively low heart rate (196). For example, processor 110 may compare the heart rate indicated by the sensed electrical activity to a threshold value or threshold range determined to be indicative of a low heart rate. In one example, processor 110 of INS 26 may classify any heart rate below approximately 30 BPM, such as, between approximately 20 to approximately 30 BPM, as a low heart rate. The threshold value or threshold range can be predetermined and stored in memory 112 (FIG. 7). In other examples, the threshold value or threshold range can be dynamic and can change based on the historic heart rate of patient 12. For example, the threshold value that indicates a low heart rate can be a mean, median, or lowest heart rate for a predetermined time range preceding the detection of the EMD state.

If processor 110 determines that the heart rate indicated by the sensed electrical activity is not a "low" heart rate, then processor 110 evaluates one or more indicators of increased sympathetic nervous system activity to determine if the indicators reflect increased or overexcited sympathetic nervous system activity (198). As described above, suitable indicators of increased sympathetic activity may include sensed nerve activity and/or heart rate variability. In some examples, processor 119 may analyze the heart rate of patient 12 previously determined to not be a "low" heart rate to determine whether the heart rate indicated by the sensed electrical signals is a relatively high or elevated heart rate. As described above, a "high" heart rate (e.g., a heart rate greater than approximately 100 BPM, such as, approximately 100 to approximately 120 BPM, may be an indicator of increased or overexcited sympathetic nervous system activity. As with determining whether a determined heart rate of patient 12 is low, processor 110 can determine whether the heart rate indicated by the sensed electrical cardiac activity is relatively high by comparing the heart rate to a threshold value or threshold range determined to be indicative of a relatively high heart rate. The threshold value or threshold range can be predetermined and stored in memory 112 (FIG. 7). In other examples, the threshold value or threshold range can be dynamic and can change based on the historic heart rate of patient 12. For example, the threshold value that indicates a relatively high heart rate can be a mean, median, or peak heart rate for a predetermined time range preceding the detection of the EMD state.

If processor 110 determines that that the one or more indicators of increased sympathetic activity (198) indicate that the EMD state is associated with increased sympathetic nervous system activity, processor 110 controls stimulation generator 114 (FIG. 7) to generate and deliver electrical stimulation to patient 12 that is configured to decrease sympathetic activity (206). In one example, INS 26 delivers electrical stimulation having a pulse rate of approximately 10 Hz to approximately 80 Hz, and a voltage amplitude of approximately 3 volts to approximately 6 volts to one or more target sites to decrease sympathetic activity. Other example stimulation parameter values are contemplated.

If processor 110 determines that the heart rate indicated by the sensed electrical signals is a relatively "low" heart rate, thereby indicating that the detected EMD state may be associated with overexcitation of the parasympathetic nervous system, processor 110 may initially determine that the autonomic nervous system activity associated with the EMD state includes vagal overexcitation or overexcitation of another parasympathetic nerve (200). Vagal nerve overexcitation is referenced herein for purposes of example only. Processor 110 may arrive at a similar determination if the indicator of increased sympathetic activity (198) does not indicate increased sympathetic nervous system activity after a determination that the heart of patient 12 is not a "low" heart rate. To verify the vagal overexcitation, similar to that described above, processor 110 may analyze one or more monitored parameters that may be used as indicators of overexcited or increased sympathetic activity (202). The indicator of increased sympathetic nervous system activity (202) may be the same or different from the indicator of increased sympathetic activity (198) analyzed by processor 110 after it was determined that the sensed electrical activity of heart 14 did not indicate a relatively "low" heart rate. In some examples, processor 110 may additionally or alternatively analyze one or more monitored parameters that may be used as indicators of overexcited or increased parasympathetic activity, e.g., to verify detected vagal overexcitation (200).

If processor 110 determines that the indicator of increased sympathetic nervous system activity (202) reflects increased sympathetic nervous system activity, processor 110 controls stimulation generator 114 to generate and deliver electrical stimulation to patient 12 that is configured to decrease sympathetic activity (206). Conversely, if the indicator of sympathetic nervous system activity (202) does not reflect increased sympathetic nervous system activity, processor 110 can control stimulation generator 114 to deliver electrical stimulation to patient 12 that is configured to increase sympathetic activity (204). In one example, stimulation generator 114, under the control of processor 110, generates and delivers electrical stimulation having a frequency (e.g., a pulse rate) of greater than approximately 100 Hz, and a voltage amplitude of approximately 5 volts to approximately 10 volts to one or more target sites to increase sympathetic activity. Other example stimulation parameter values are contemplated. In some examples, this relatively high frequency stimulation may be initially delivery to "wake-up" or bring the heart out of the detected EMD state, e.g., by inducing one or more mechanical contractions. Similar to that described above, after a set period of time, INS 26 can terminate delivery of the high frequency stimulation and deliver a lower intensity stimulation, e.g., to avoid undesirable side-effects from the high intensity stimulation to the same or a different tissue site as the high frequency stimulation.

Whether INS 26 delivers stimulation to decrease sympathetic activity sympathetic activity (206) or increase sympathetic activity (204) based on the autonomic nervous system activity determined to be associated with the EMD state of heart 14, after delivery of the stimulation, e.g., for some predetermined time period, processor 110 may determine whether heart 14 is still in an EMD state (208). If the delivered stimulation did not terminate the EMD state (e.g., heart 14 is not contracting in a physiologically significant manner), processor 110 may modify one or more stimulation parameter values from the previously delivered stimulation (212) and deliver the modified stimulation to patient 12 (214). As described above, in some examples, in order to modify the one or more stimulation parameter values to find an effective neurostimulation therapy that terminates the EMD state, processor 110 may be configured to sequentially select a therapy program from a predetermined set of therapy programs, e.g., defining different stimulation signals, electrode combinations, and electrode locations. In some examples, INS 26 may deliver stimulation according to each program for between approximately 5 seconds to approximately 60 seconds, and check whether heart 14 is still in the EMD state after each therapy delivery session with the selected therapy program. If a therapy program is found to be effective in terminating the EMD state, processor 110 can continue to control stimulation generator 114 to generate and deliver therapy according to that therapy program until the EMD state is terminated.

Once the EMD state has been terminated, processor 110 may assess the cardiac and/or autonomic nervous system state of patient 12 (210). While the EMD state of patient 12 may be successfully terminated, the cardiac state and/or autonomic state of patient may not have returned to a desirable state, e.g., a state in which the likelihood of a subsequent EMD state is relatively low. For example, the heart rate of patient 12 may be elevated or depressed from that of a desired heart rate. In some examples, the monitored heart rate may display an undesirable level of variability. In some examples, processor 110 may determined that the parasympathetic and/or sympathetic nervous system activity remains depressed or overexcited. Based on the cardiac and autonomic assessment, processor 110 can control stimulation generator 114 to generate and deliver stimulation to manage cardiac and/or autonomic state when determined to be undesirable. As described above, in some examples, INS 26 may continue to delivery therapy to patient 12 for approximately 30 seconds to approximately 120 minutes after the EMD state has been terminated as a follow-up therapy to help assure that EMD state does not imminently reappear. The stimulation therapy delivered by INS 26 can initiate at a relatively large amplitude or duty cycle "on" time to treat an EMD state. Then, after EMD is resolved, the stimulation therapy may be adjusted, e.g., to remain at a relatively lower amplitude and/or duty cycle or even deactivated.

In some aspects, examples of the disclosure may include a method comprising determining whether a heart of a patient is in an electromechanical dissociation state; determining autonomic nervous system activity of the patient associated with the electromechanical dissociation state; and delivering electrical stimulation to the patient based on the determined autonomic nervous system activity of the patient associated with the electromechanical dissociation state.

In one example, determining the autonomic nervous system activity of the patient comprises at least one of determining whether sympathetic nervous system activity of the patient is overexcited or depressed, or determining whether parasympathetic nervous system activity of the patient is overexcited or depressed.

In one example, the example method further comprising delivering first electrical stimulation therapy to the patient to increase sympathetic nervous system activity upon determining that the heart is in the electromechanical dissociation state, wherein delivering electrical stimulation to the patient based on the determined autonomic activity level comprises delivering second electrical stimulation therapy to the patient based on the determined autonomic activity after delivery of the first electrical stimulation. In some examples, the first electrical stimulation has a frequency greater than approximately 100 hertz. In some examples, the second electrical stimulation therapy is configured to reduce sympathetic nervous system activity.

In one example, determining autonomic activity of the patient comprising detecting overexcited sympathetic nervous system activity of the patient, and wherein delivering electrical stimulation to the patient based on the determined autonomic activity of the patient associated with the electromechanical dissociation state comprises delivering electrical stimulation configured to decrease sympathetic nervous system activity to the patient.

In one example, determining autonomic activity of the patient comprising detecting depressed sympathetic nervous system activity of the patient, and wherein delivering electrical stimulation to the patient based on the determined autonomic activity of the patient associated with the electromechanical dissociation state comprises delivering electrical stimulation configured to increase sympathetic nervous system activity to the patient.

In one example, determining the autonomic nervous system activity of the patient comprises determining the autonomic nervous system activity of the patient based on at least one of sensed electrical activity of the heart or sensed electrical nerve activity.

In one example, determining whether the heart of the patient is in the electromechanical dissociation state comprises determining whether the heart of the patient is in the electromechanical dissociation state based on the at least one sensed physiological parameter. In some examples, the at least one physiological parameter of the patient comprises one or more parameters indicative of mechanical contraction of the heart.

In some aspects, examples of the disclosure may include a medical system comprising a stimulation generator and a processor. The processor determines whether a heart of a patient is in an electrical mechanical dissociation state, determines autonomic nervous system activity of the patient associated with the electromechanical dissociation state, and controls the stimulation generator to deliver electrical stimulation to the patient based on the determined autonomic nervous system activity of the patient associated with the electromechanical dissociation state.

In one example, the processor determines the autonomic nervous system activity of the patient by at least one of determining whether sympathetic nervous system activity of the patient is overexcited or depressed, or determining whether parasympathetic nervous system activity of the patient is overexcited or depressed.

In one example, the processor controls the stimulation generator to deliver first electrical stimulation therapy to the patient to increase sympathetic nervous system activity upon determining that the heart is in the electromechanical dissociation state, and subsequently controls the stimulation generator to deliver the electrical stimulation to the patient based on the determined autonomic activity level by delivering second electrical stimulation therapy to the patient based on the determined autonomic activity after the delivery of the first electrical stimulation. In some examples, the first electrical stimulation comprises a frequency greater than approximately 100 hertz. In some examples, the second electrical stimulation therapy delivered to the patient is configured to reduce sympathetic nervous system activity.

In one example, the processor determines autonomic activity of the patient by at least detecting overexcited sympathetic nervous system activity of the patient, and wherein the processor controls the stimulation generator to deliver electrical stimulation to the patient based on the determined autonomic activity of the patient associated with the electromechanical dissociation state by at least delivering electrical stimulation configured to decrease sympathetic nervous system activity to the patient.

In one example, the processor determines autonomic activity of the patient by at least detecting depressed sympathetic nervous system activity of the patient, and wherein the processor controls the stimulation generator to deliver electrical stimulation to the patient based on the determined autonomic activity of the patient associated with the electromechanical dissociation state by at least delivering electrical stimulation configured to increase sympathetic nervous system activity to the patient.

In one example, the medical system further comprises a sensor that senses at least one of electrical activity of the heart or electrical nerve activity, wherein the processor determines the autonomic activity of the patient based on at least one of the sensed electrical activity of the heart or the sensed electrical nerve activity.

In one example, the medical system further comprises a sensor that senses at least one physiological parameter of the patient indicative of mechanical contraction of the heart, wherein the processor determines whether the heart of the patient is in an electrical mechanical dissociation state based on the at least one sensed physiological parameter of the patient, In some aspects, examples of the disclosure may include a medical system comprising means for determining whether a heart of a patient is in an electromechanical dissociation state; means for determining autonomic activity of the patient associated with the electromechanical dissociation state; and means for delivering electrical stimulation to the patient based on the determined autonomic activity of the patient associated with the electromechanical dissociation state.

In one example, the means for determining the autonomic nervous system activity of the patient comprises at least one of means for determining whether the sympathetic nervous system activity of the patient is overexcited or depressed, or means for determining whether the parasympathetic nervous system activity of the patient is overexcited or depressed.

In some aspects, examples of the disclosure may include a method of treating an electromechanical disassociation state of a heart of a patient, wherein the method is characterized by implanting a medical device system in a patient, where the medical device system comprises a stimulation generator, and a processor that determines whether a heart of a patient is in an electrical mechanical dissociation state, determines autonomic nervous system activity of the patient associated with the electromechanical dissociation state upon determining that the heart is in the electromechanical dissociation state, and controls the stimulation generator to deliver electrical stimulation to the patient based on the determined autonomic nervous system activity of the patient associated with the electromechanical dissociation state.

In one example, the medical device system further comprise a sensor that generate a signal indicative of the at least one physiological parameter of the patient indicative of mechanical contraction of the heart, wherein the processor determines whether the heart of the patient is in the electrical mechanical dissociation state based on the signal.

Although the examples provided are primarily described with respect to implantable medical devices and systems, examples are not limited as such. In some examples, one or more of the described techniques may be incorporated into an external device, such as, e.g., as external defibrillator, to determine if a patient's heart is in an EMD state and provide therapy to patient based on the determination. In such cases, electrical stimulation may be provided to a patient via one or more external electrodes positioned proximate an appropriate tissue site of the patient to treat the EMD state as described herein.

The techniques described in this disclosure, including those attributed to ICD 16, INS 26, programmer 24, ICD 82 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 90 of ICD 16, processor 110 of INS 26, and/or processor 130 of programmer 24, any one or more parts of the techniques described herein may be implemented by a processor of one of the devices 16, 26, programmer 24 or another computing device, alone or in combination with ICD 16, INS 26 or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following claims.

The invention claimed is:

1. A method comprising:
sensing at least one physiological parameter of a patient;
determining whether a heart of the patient is in an electromechanical dissociation state based on the at least one sensed physiological parameter; and
delivering electrical stimulation to a tissue site of the patient to at least one of modulate afferent nerve activity or inhibit efferent nerve activity upon determining that the heart is in the electromechanical dissociation state,
wherein the tissue site comprises at least one of a nonmyocardial tissue site or a nonvascular cardiac tissue site.

2. The method of claim 1, wherein the tissue site comprises at least one of an efferent nerve site or an afferent nerve site.

3. The method of claim 1, wherein the tissue site comprises a spinal cord of the patient.

4. The method of claim 1, wherein the tissue site comprises a tissue proximate to one or more thoracic segments.

5. The method of claim 1, wherein delivering electrical stimulation to the tissue site of the patient to at least one of modulate afferent nerve activity or inhibit efferent nerve activity upon determining that the heart is in the electromechanical dissociation state comprises delivering electrical stimulation to the tissue site of the patient to at least one of modulate afferent nerve activity or inhibit efferent nerve activity but not excite efferent nerve activity upon determining that the heart is in the electromechanical dissociation state.

6. The method of claim 1, further comprising withholding delivery of electrical stimulation to the tissue site when the electromechanical dissociation state is not determined.

7. The method of claim 1, wherein the at least one physiological parameter of the patient comprises one or more parameters indicative of mechanical contraction of the heart.

8. The method of claim 7, wherein the at least one physiological parameter comprises at least one of blood pressure, blood flow, respiratory rate, tissue perfusion, pulsatility, blood oxygen concentration, blood sugar concentration, blood pH or blood calcium concentration.

9. The method of claim 1, wherein determining whether the heart of the patient is in the electromechanical dissociation state comprises comparing the at least one physiological parameter of the patient to a threshold value that is indicative of the electromechanical dissociation state.

10. The method of claim 1, further comprising sensing delivery of at least one of cardioversion or defibrillation therapy to the heart, wherein delivering electrical stimulation to a tissue site of the patient to at least one of modulate afferent nerve activity or inhibit efferent nerve activity upon determining that the heart is in the electromechanical dissociation state comprises delivering the electrical stimulation within approximately 10 seconds of the delivery of the at least one of cardioversion or defibrillation therapy to the heart.

11. The method of claim 1, wherein delivering electrical stimulation to a tissue site of the patient comprises delivering relatively high frequency electrical stimulation to the tissue site for a first time period and then delivering relatively low frequency electrical stimulation to the tissue site for a second time period, wherein the first time period begins before the second time period.

12. The method of claim 11, wherein the high frequency electrical stimulation has a frequency in a range of approximately 50 hertz to approximately 100 hertz.

13. The method of claim 11, wherein the first time period is less than or approximately equal to one minute but greater than zero.

14. A medical system comprising:
a sensor that senses at least one physiological parameter of a patient;
a stimulation generator; and
a processor that determines whether a heart of the patient is in an electrical mechanical dissociation state based on the at least one sensed physiological parameter and controls the stimulation generator to deliver electrical stimulation to a tissue site of the patient to at least one of modulate afferent nerve activity or inhibit efferent nerve activity upon determining that the heart is in the electrical mechanical dissociation state, wherein the tissue site comprises at least one of a nonmyocardial tissue site or a nonvascular cardiac tissue site.

15. The medical system of claim 14, wherein the tissue site comprises at least one of an efferent nerve site or an afferent nerve site.

16. The medical system of claim 14, wherein the processor controls the stimulation generator to deliver electrical stimulation to the tissue site of the patient to at least one of modulate afferent nerve activity or inhibit efferent nerve activity but not excite efferent nerve activity upon determining that the heart is in the electrical mechanical dissociation state.

17. The medical system of claim 14, wherein the processor controls the stimulation generator to withhold delivery of electrical stimulation to the tissue site when the electromechanical dissociation state is not determined.

18. The medical system of claim 14, wherein the at least one physiological parameter of the patient is indicative of mechanical contraction of the heart.

19. The medical system of claim 14, wherein the at least one physiological parameter comprises at least one of blood pressure or blood flow, respiratory rate, tissue perfusion, pulsatility, blood oxygen concentration, blood sugar concentration, blood pH, or blood calcium concentration.

20. The medical system of claim 14, wherein the processor determines whether the heart is in the electromechanical dissociation state based at least in part on a comparison of the at least one physiological parameter of the patient to a threshold value.

21. The medical system of claim 14, wherein the stimulation generator comprises a first stimulation generator, the system further comprising a second stimulation generator that delivers at least one of cardioversion or defibrillation therapy to the heart of the patient, wherein the processor controls the first stimulation generator deliver electrical stimulation to a tissue site of the patient to at least one of modulate afferent nerve activity or inhibit efferent nerve activity within approximately 10 seconds of delivery of the at least one of cardioversion or defibrillation therapy to the heart by the second stimulation generator.

22. The medical system of claim 14, wherein the processor controls the stimulation generator to generate and deliver a relatively high frequency electrical stimulation delivered to the tissue site for a first time period immediately following a determination that the heart is in the electromechanical disassociation state and deliver a relatively low frequency electrical stimulation delivered to the tissue site for a second time period, wherein the first time period begins before the second time period.

23. The medical system of claim 22, wherein the high frequency electrical stimulation has a frequency between approximately 50 hertz to approximately 100 hertz.

24. A medical system comprising:
means for sensing at least one physiological parameter of a patient;
means for determining whether a heart of the patient is in an electrical mechanical dissociation state of a heart of the patient based on the at least one sensed physiological parameter; and
means for delivering electrical stimulation to a tissue site of the patient to at least one of modulate afferent nerve activity or inhibit efferent nerve activity upon determining that the heart is in the electrical mechanical dissociation state,
wherein the tissue site comprises at least one of a nonmyocardial tissue site or a nonvascular cardiac tissue site.

25. The medical system of claim 24, wherein the means for delivering electrical stimulation to the tissue site delivers a relatively high frequency electrical stimulation delivered to the tissue site for a first time period immediately following a determination that the heart is in the electromechanical disassociation state and delivers a relatively low frequency electrical stimulation delivered to the tissue site for a second time period, wherein the first time period begins before the second time period.

26. A method of treating an electromechanical disassociation state of a heart of a patient, wherein the method is characterized by implanting a medical device system in a patient, where the medical device system comprises a stimulation generator and a processor that determines whether the heart of the patient is in the electrical mechanical dissociation state based on at least one sensed physiological parameter and controls the stimulation generator to deliver electrical stimulation to a tissue site of the patient to at least one of modulate afferent nerve activity or inhibit efferent nerve activity upon determining that the heart is in the electrical mechanical dissociation state, wherein the tissue site comprises at least one of a nonmyocardial tissue site or a nonvascular cardiac tissue site.

27. The method of claim 26, wherein the medical device system further comprise a sensor that generate a signal indicative of the at least one physiological parameter of the patient, wherein the processor determines whether the heart of the patient is in the electrical mechanical dissociation state based on the signal.

* * * * *